US012559468B2

(12) United States Patent
Shirai et al.

(10) Patent No.: US 12,559,468 B2
(45) Date of Patent: Feb. 24, 2026

(54) METHOD FOR PRODUCING ORGANIC COMPOUND

(71) Applicants: DAIKIN INDUSTRIES, LTD., Osaka (JP); NATIONAL UNIVERSITY CORPORATION SHIZUOKA UNIVERSITY, Shizuoka (JP)

(72) Inventors: Atsushi Shirai, Osaka (JP); Yoshichika Kuroki, Osaka (JP); Nobuyuki Mase, Shizuoka (JP)

(73) Assignees: DAIKIN INDUSTRIES, LTD., Osaka (JP); NATIONAL UNIVERSITY CORPORATION SHIZUOKA UNIVERSITY, Shizuoka (JP)

( * ) Notice: Subject to any disclaimer, the term of this patent is extended or adjusted under 35 U.S.C. 154(b) by 1150 days.

(21) Appl. No.: 17/396,088

(22) Filed: Aug. 6, 2021

(65) Prior Publication Data

US 2021/0371391 A1 Dec. 2, 2021

Related U.S. Application Data

(63) Continuation of application No. PCT/JP2020/004995, filed on Feb. 7, 2020.

(30) Foreign Application Priority Data

Feb. 8, 2019 (JP) ................................ 2019-022160

(51) Int. Cl.

| | |
|---|---|
| ***C07D 317/16*** | (2006.01) |
| ***C07C 31/38*** | (2006.01) |
| ***C07D 307/10*** | (2006.01) |
| ***C08J 3/09*** | (2006.01) |
| ***C08L 27/12*** | (2006.01) |

(52) U.S. Cl.

CPC ............ *C07D 317/16* (2013.01); *C07C 31/38* (2013.01); *C07D 307/10* (2013.01); *C08J 3/09* (2013.01); *C08L 27/12* (2013.01); *C08J 2327/12* (2013.01)

(58) Field of Classification Search

CPC .... C07D 317/16; C07D 307/10; C07C 31/38; C08J 3/09; C08J 2327/12; C08L 27/12

See application file for complete search history.

(56) References Cited

U.S. PATENT DOCUMENTS

| | | | | |
|---|---|---|---|---|
| 3,883,663 | A | 5/1975 | Moore et al. | |
| 3,987,203 | A | 10/1976 | Moore et al. | |
| 5,393,524 | A | 2/1995 | Quay | |
| 5,558,094 | A | 9/1996 | Quay | |
| 5,804,650 | A | 9/1998 | Tsuda et al. | |
| 6,177,532 | B1 | 1/2001 | Otani et al. | |
| 8,889,253 | B2 * | 11/2014 | Kekicheff ................ | B05D 3/02 428/220 |
| 2002/0128411 | A1 | 9/2002 | Navarrini et al. | |
| 2004/0198702 | A1 | 10/2004 | Petrova et al. | |
| 2011/0098511 | A1 | 4/2011 | Kagawa et al. | |

(Continued)

FOREIGN PATENT DOCUMENTS

| | | |
|---|---|---|
| CN | 1121416 | 9/2003 |
| CN | 103797024 | 5/2014 |

(Continued)

OTHER PUBLICATIONS

Puts, Jan. 2019, Chemical Reviews vol. 119(3), 1763-1805. (Year: 2019).*

(Continued)

*Primary Examiner* — D Margaret M Seaman

(74) *Attorney, Agent, or Firm* — Wenderoth, Lind & Ponack, L.L.P.

(57) ABSTRACT

An object of the present disclosure is to provide a method for producing an organic compound, and a composition. The object is achieved by a method for producing a compound represented by formula (1):

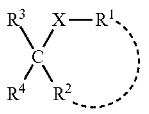

(1)

wherein X represents —O—, an optionally substituted imino group, or —S—, $R^1$ represents a hydrogen atom or a hydrocarbyl group optionally having at least one substituent, and $R^2$ represents a hydrogen atom or a monovalent organic group, or $R^1$ and $R^2$, together with X and one carbon atom respectively adjacent to $R^1$ and $R^2$, may form a heterocyclic ring optionally having at least one substituent, $R^3$ represents a hydrogen atom or a monovalent organic group, and $R^4$ represents $—CF_2CH_3$ or $—CH_2CHF_2$; the method including step A of reacting a compound represented by formula (2):

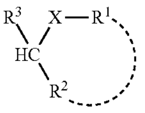

(2)

wherein the alphabetical symbols are as defined above, with vinylidene fluoride under light irradiation.

3 Claims, 28 Drawing Sheets

(56) References Cited

U.S. PATENT DOCUMENTS

| | | | |
|---|---|---|---|
| 2013/0115190 A1 | 5/2013 | Hiebert et al. |
| 2013/0344030 A1 | 12/2013 | Steadman et al. |
| 2015/0094432 A1 | 4/2015 | Leduc et al. |
| 2015/0125422 A1 | 5/2015 | Hiebert et al. |
| 2015/0361132 A1 | 12/2015 | Aciro et al. |
| 2016/0220633 A1 | 8/2016 | Aciro et al. |
| 2017/0190734 A1 | 7/2017 | Aciro et al. |
| 2019/0237804 A1 | 8/2019 | Shi et al. |

FOREIGN PATENT DOCUMENTS

| | | | |
|---|---|---|---|
| EP | 0 143 864 | | 6/1985 |
| EP | 0495823 | * | 4/1994 |
| JP | 48-20111 | | 6/1973 |
| JP | 5-123559 | | 5/1993 |
| JP | 5-177122 | | 7/1993 |
| JP | 2002-530359 | | 9/2002 |
| JP | 2002-332275 | | 11/2002 |
| JP | 2013-224266 | | 10/2013 |
| JP | 2014-5217 | | 1/2014 |
| JP | 2015-513545 | | 5/2015 |
| JP | 2015-525221 | | 9/2015 |
| JP | 2017-19743 | | 1/2017 |
| JP | 2017-213519 | | 12/2017 |
| JP | 2018-127398 | | 8/2018 |
| JP | 2018-130648 | | 8/2018 |
| KR | 101785342 | | 11/2017 |
| WO | 2009/154135 | | 12/2009 |
| WO | 2012/150256 | | 11/2012 |
| WO | 2013/078468 | | 5/2013 |
| WO | 2017/132023 | | 8/2017 |
| WO | 2017/216280 | | 12/2017 |
| WO | 2018/094843 | | 5/2018 |

OTHER PUBLICATIONS

Partial Supplementary European Search Report issued Oct. 19, 2022 in correpsonding European Patent Application No. 20752488.5.
W.A. Smit et al., "Organic Synthesis", The Science Behind the Art, The Royal Society of Chemistry, pp. 41-43, 1998, with English language translation.
International Preliminary Report on Patentability issued Ausgust 10, 2021 in corresponding International (PCT) Patent Application No. PCT/JP2020/004995.
Extended European Search Report issued Dec. 12, 2023 in corresponding European Patent Application No. 23192931.6.
Extended European Search Report dated Jan. 25, 2023 issued in European Application No. 20752488.5.
Cuntian Pu, "Fine Chemical Process and Equipment", Teaching Books for Colleges and Universities, Chemical Industry Press, New Catalogue No. 039, pp. 48-51 (1996).
Jianguo Chen et al., "Synthesis of Cyclic Ethers with Fluorinated Side Chains", Inorganic Chemistry, 1996, vol. 35, pp. 1590-1601.
File Registry (STN), Jun. 27, 2018, RN 2227771-38-0, etc., pp. 1-16.
Yong Xu et al., "Synthesis of difluoromethyl substituted lysophosphatidic acid analogues", Tetrahedron, 2004, vol. 60, pp. 43-49.
Klaus Burger et al., "Efficient stereoconservative syntheses of 4,4-difluoro-2-hydroxybutyric acids from (S)- and (R)-malic and (S)- and (R)-citramalic acid", Journal of Fluorine Chemistry, 2000, vol. 102, pp. 317-321.
Yong Guo et al., "The Reaction and Its Product Conversion of Difluorodiiodomethane with Ethyl Vinyl Ether", Acta Chimica Sinica, 2001, vol. 59, No. 10, pp. 1722-1729.
Stojan Stavber et al., "Room-Temperature Fluorination of 1-Phenylacetylenes with Cesium Fluoroxysulfate", Journal of Organic Chemistry, 1987, vol. 52, pp. 5022-5025.
Masato Yoshida et al., "Convenient preparation of difluoromethylene-functionalized compounds from chlorodifluoroacetic acid", Journal of Fluorine Chemistry, 1994, vol. 68, pp. 33-38.
File Registry (STN), Jan. 3, 2018, RN 2168664-77-3, etc., pp. 1-43.
Ryo Mogi et al., "Synthesis of 1,1-difluoroethylsilanes and their application for the introduction of the 1,1-difluoroethyl group", Journal of Fluorine Chemistry, 2007, vol. 128, pp. 1098-1103.
Mikhail D. Kosobokov et al., "Difluorohomologation of Ketones", Organic Letters, 2015, vol. 17, pp. 760-763.
Zuyong Deng et al., "Nucleophilic 1,1-Difluoroethylation with Fluorinated Phosphonium Salt", Journal of Organic Chemistry, 2016, vol. 81, pp. 12084-12090.
Yang Ran et al., "Visible Light Induced Oxydifluoromethylation of Styrenes with Difluoromethyltriphenylphosphonium Bromide", Journal of Organic Chemistry, 2016, vol. 81, pp. 7001-7007.
2024 ACS on STN, pp. 1-25, Answers 1 through 65, for example, RN 2227771-38-0 (Jun. 27, 2018), etc.
International Search Report issued Apr. 21, 2020 in International (PCT) Application No. PCT/JP2020/004995.
Vorberg et al., "Effect of Partially Fluorinated N-Alkyl-Substituted Piperidine-2-carboxamides on Pharmacologically Relevant Properties", Chem Med Chem, 2016, vol. 11, pp. 2216-2239.
Arai et al., "Oxydifluoromethylation of Alkenes by Photoredox Catalysis: Simple Synthesis of $CF_2H$-Containing Alcohols", Chemistry A European Journal, 2016, vol. 22, pp. 1262-1265.
Církva et al., "Radical addition reactions of fluorinated species. Part 7. Highly selective two-step synthesis of 1-(polyfluoroalkyl)ethane-1,2-diols; regioselectivity of the additions of methylated 1,3-dioxolanes to perfluoroolefins", Journal of Fluorine Chemistry, 1999, vol. 94, pp. 141-156.
CAS RN 1250833-69-2 and CAS RN 1250193-11-3, Nov. 2010, pp. 1-2.

* cited by examiner 2,3,3,3-Tetrafluoropropylene
Liquid Medium: 1,3-Dioxolane

1-Bromo-1-fluoroethylene
Liquid Medium: Water

METHOD FOR PRODUCING ORGANIC COMPOUND

TECHNICAL FIELD

The present disclosure relates to a method for producing an organic compound (specifically, a method for producing an organic compound containing heteroatoms; more specifically, a method for producing an organic compound containing heteroatoms under light irradiation), and a composition.

BACKGROUND ART

As a method for producing an organic compound (specifically, a method for producing an organic compound containing heteroatoms), more specifically a method for producing an organic compound containing heteroatoms under light irradiation, for example, Non-patent Literature 1 reports 1-(polyfluoroalkyl)ethane-1,2-diol under UV light irradiation.

CITATION LIST

Non-Patent Literature

NPL 1: Vladimir Cirkva et al., Journal of Fluorine Chemistry 94 (1999): pp. 141-156

SUMMARY

The present disclosure provides the following as a solution to achieve the object.

Item 1. A method for producing a compound represented by formula (1):

(1)

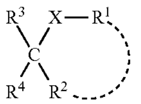

wherein

X represents —O—, an optionally substituted imino group, or —S—, $R^1$ represents a hydrogen atom or a hydrocarbyl group optionally having at least one substituent, and $R^2$ represents a hydrogen atom or a monovalent organic group, or $R^1$ and $R^2$, together with X and one carbon atom respectively adjacent to $R^1$ and $R^2$, may form a heterocyclic ring optionally having at least one substituent, $R^3$ represents a hydrogen atom or a monovalent organic group, and $R^4$ represents $-CF_2CH_3$ or $-CH_2CHF_2$;

the method comprising step A of reacting a compound represented by formula (2):

(2)

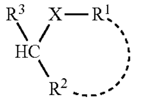

wherein alphabetical symbols are as defined above, with vinylidene fluoride under light irradiation.

Advantageous Effects of Invention

The present disclosure provides a novel method for producing an organic compound (specifically a method for producing an organic compound containing heteroatoms, more specifically a novel method for producing an organic compound containing heteroatoms under light irradiation).

DESCRIPTION OF EMBODIMENTS

Terms

Figure 1:
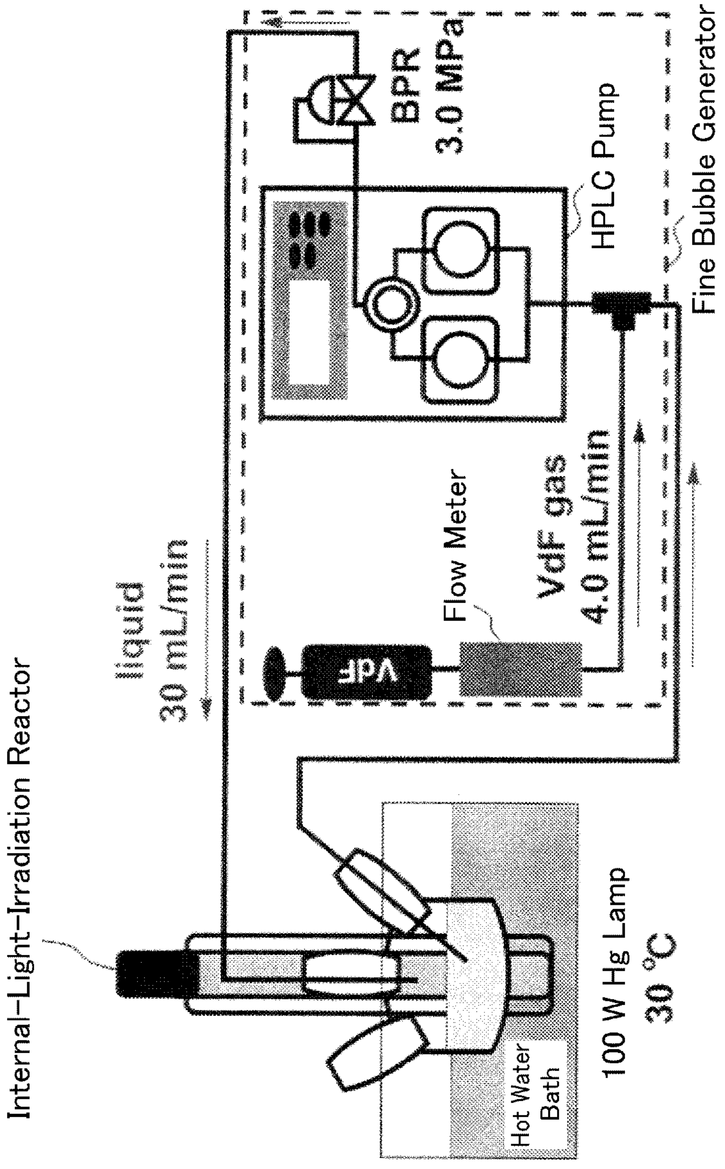
FIG. 1 shows an overview of an apparatus used in the production method according to the present disclosure (Examples 1 to 9).

The symbols and abbreviations in this specification can be understood in the sense normally used in the technical field to which the present disclosure pertains in the context of this specification, unless otherwise indicated. The term "comprising" is used in this specification with the intent of encompassing the terms "consisting essentially of" and "consisting of."

Unless otherwise indicated, the steps, treatments, or operations described in this specification can be performed at room temperature.

In this specification, "room temperature" means a temperature within the range of 10 to 40° C.

In this specification, the expression "Cn-Cm" (wherein n and m each represent a number) denotes a carbon number greater than or equal to n and less than or equal to m, as can be ordinarily understood by those skilled in the art.

As can be understood by those skilled in the art based on common technical knowledge, the term "content" and the term "purity" can be used interchangeably herein, depending on the context.

In accordance with the definition from the Technical Committee on Fine Bubble Technology (2013) of the International Organization for Standardization (ISO), the term "fine bubbles" in this specification means bubbles with a diameter of 100 μm or less. The term "microbubbles" means bubbles with a diameter of 1 to 100 μm; and the term "ultrafine bubbles" means bubbles with a diameter of 1 μm or less. The term "microbubbles" and the term "ultrafine bubbles" are both encompassed in the term "fine bubbles."

In the specification, the term "halogen atom" includes, for example, fluorine, chlorine, bromine, and iodine.

In the specification, unless otherwise indicated, "organic group" refers to a group containing at least one carbon atom as its constituent atom.

In the specification, unless otherwise indicated, "monovalent organic group" includes a hydrocarbyl group.

In the specification, unless otherwise indicated, examples of organic groups include a hydrocarbyl group, a hydrocarbyloxy group (e.g., an alkoxy group), an ester group, an ether group, a hydrocarbyloxy group (e.g., an alkoxy group), an ester group, an ether group (or a group containing an ether bond), an acyl group, and a heterocyclic group (e.g., a heteroaryl group and a non-aromatic heterocyclic group).

The organic group can be, for example, a monovalent organic group.

In the specification, unless otherwise indicated, a monovalent organic group refers to, for example, a hydrocarbyl group.

In the specification, unless otherwise indicated, "hydrocarbyl group" refers to a group containing at least one carbon atom and at least one hydrogen atom as its constituent atoms. The hydrocarbyl group is also referred to as a "hydrocarbon group."

In the specification, unless otherwise indicated, examples of hydrocarbyl groups include an aliphatic hydrocarbyl group optionally substituted with at least one aromatic hydrocarbyl group (e.g., a benzyl group), and an aromatic hydrocarbyl group optionally substituted with at least one aliphatic hydrocarbyl group (aryl group).

In the specification, unless otherwise indicated, an aliphatic hydrocarbyl group can be a linear aliphatic hydrocarbyl group, a branched aliphatic hydrocarbyl group, a cyclic aliphatic hydrocarbyl group, or a combination thereof.

In the specification, unless otherwise indicated, an aliphatic hydrocarbyl group can be a saturated or unsaturated aliphatic hydrocarbyl group.

In the specification, unless otherwise indicated, examples of aliphatic hydrocarbyl groups include an alkyl group, an alkenyl group, an alkynyl group, and a cycloalkyl group.

In the specification, unless otherwise indicated, examples of alkyl groups include linear or branched alkyl groups having 1 to 10 carbon atoms, such as methyl, ethyl, propyl (e.g., propyl, and isopropyl), butyl (e.g., n-butyl, isobutyl, sec-butyl, and tert-butyl), pentyl (e.g., n-pentyl, isopentyl, and neopentyl), and hexyl.

In the specification, unless otherwise indicated, examples of alkenyl groups include linear or branched alkenyl groups having 2 to 10 carbon atoms, such as vinyl, 1-propenyl, isopropenyl, 2-methyl-1-propenyl, 1-butenyl, 2-butenyl, 3-butenyl, 2-ethyl-1-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, and 5-hexenyl.

In the specification, unless otherwise indicated, examples of alkynyl groups include linear or branched alkynyl group having 2 to 6 carbon atoms, such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, and 5-hexynyl.

In the specification, unless otherwise indicated, examples of cycloalkyl groups include cycloalkyl groups having 3 to 8 carbon atoms, such as a cyclopentyl group, a cyclohexyl group, and a cycloheptyl group.

In the specification, unless otherwise indicated, examples of aromatic hydrocarbyl groups (aryl groups) include a phenyl group, a naphthyl group, a phenanthryl group, an anthryl group, and a pyrenyl group.

In the specification, unless otherwise indicated, an alkoxy group refers to, for example, a group represented by RO— (wherein R represents an alkyl group).

In the specification, unless otherwise indicated, an ester group refers to an organic group having an ester bond (i.e., —C(═O)—O— or —O—C(═O)—). Examples thereof include a group represented by formula: $RCO_2$— (wherein R represents an alkyl group) and a group represented by formula: $R^a$—$CO_2$—$R^b$— (wherein $R^a$ represents an alkyl group, and $R^b$ represents an alkylene group).

In the specification, unless otherwise indicated, "ether group" or "ether-bond-containing group" refers to a group having an ether bond (—O—).

Examples of ether groups and ether-bond-containing groups include polyether groups. Examples of polyether groups include a group represented by formula: $R^a$—(O—$R^b$)$_n$— (wherein $R^a$ represents an alkyl group, $R^b$, in each occurrence, may be the same or different and represents an alkylene group, and n represents an integer of 1 or more). An alkylene group refers to a divalent group formed by removing one hydrogen atom from an alkyl group. Examples of ether groups or ether-bond-containing groups include hydrocarbyl ether groups. A hydrocarbyl ether group refers to a hydrocarbyl group having at least one ether bond inside and/or at the end (or the base) of the group. The "hydrocarbyl group having at least one ether bond" can be a hydrocarbyl group into which at least one ether bond is inserted. Examples thereof include hydrocarbyloxy groups (e.g., a benzyloxy group).

Examples of hydrocarbyl groups having at least one ether bond include an alkyl group having at least one ether bond. The alkyl group having at least one ether bond can be an alkyl group having at least one ether bond inserted. In the specification, such a group may be referred to as "alkyl ether group."

In the specification, unless otherwise indicated, "acyl group" includes an alkanoyl group. In the specification, unless otherwise indicated, an alkanoyl group is, for example, a group represented by RCO— (wherein R represents an alkyl group).

In the specification, unless otherwise indicated, examples of heteroaryl groups include κ-membered or 6-membered heteroaryl groups, and groups formed by these groups fused with a benzene ring.

In the specification, unless otherwise indicated, examples of 5- or 6-membered monocyclic aromatic heterocyclic groups include 5-membered heteroaryl groups having at least one heteroatom selected from the group consisting of oxygen, sulfur, and nitrogen (e.g., one, two, or three atoms) as a ring-constituting atom, such as pyrrolyl (e.g., 1-pyrrolyl, 2-pyrrolyl, and 3-pyrrolyl), furyl (e.g., 2-furyl, and 3-furyl), thienyl (e.g., 2-thienyl, and 3-thienyl), pyrazolyl (e.g., 1-pyrazolyl, 3-pyrazolyl, and 4-pyrazolyl), imidazolyl (e.g., 1-imidazolyl, 2-imidazolyl, and 4-imidazolyl), isooxazolyl (e.g., 3-isooxazolyl, 4-isooxazolyl, and 5-isooxazolyl), oxazolyl (e.g., 2-oxazolyl, 4-oxazolyl, and 5-oxazolyl), isothiazolyl (e.g., 3-isothiazolyl, 4-isothiazolyl, and 5-isothiazolyl), thiazolyl (e.g., 2-thiazolyl, 4-thiazolyl, and 5-thiazolyl), triazolyl (e.g., 1,2,3-triazol-4-yl, and 1,2,4-triazol-3-yl), oxadiazolyl (e.g., 1,2,4-oxadiazol-3-yl, and 1,2,4-oxadiazol-5-yl), thiadiazolyl (e.g., 1,2,4-thiadiazol-3-yl, and 1,2,4-thiadiazol-5-yl), tetrazolyl, pyridyl (e.g., 2-pyridyl, 3-pyridyl, and 4-pyridyl), pyridazinyl (e.g., 3-pyridazinyl, and 4-pyridazinyl), pyrimidinyl (e.g., 2-pyrimidinyl, 4-pyrimidinyl, and 5-pyrimidinyl), and pyrazinyl.

In the specification, unless otherwise indicated, examples of heterocyclic rings include 5- to 7-membered heterocyclic rings having one to four heteroatoms selected from a nitrogen atom, a sulfur atom, and an oxygen atom, in addition to a carbon atom.

In the specification, unless otherwise indicated, examples of heterocyclic rings include non-aromatic heterocyclic rings and aromatic heterocyclic rings.

In the specification, unless otherwise indicated, examples of 5- to 7-membered heterocyclic rings having one to four heteroatoms selected from a nitrogen atom, a sulfur atom, and an oxygen atom, in addition to a carbon atom include pyrrolidine, tetrahydrofuran, tetrahydrothiophene, piperidine, tetrahydropyran, morpholine, thiomorpholine, piperazine, and hexamethyleneimine.

In the specification, unless otherwise indicated, examples of non-aromatic heterocyclic rings include 3- to 8-membered non-aromatic heterocyclic rings. Specific examples include oxirane, azetidine, oxetane, thietane, pyrrolidine, dihydrofuran, tetrahydrofuran, tetrahydrothiophene, imidazolidine, oxazolidine, isoxazoline, piperidine, dihydropyran, tetrahydropyran, tetrahydrothiopyran, morpholine, thiomorpholine, piperazine, dihydrooxazine, tetrahydrooxazine, dihydropyrimidine, tetrahydropyrimidine, azepane, oxepane, thiepane, oxazepane, thiazepane, azocane, oxocane, thiocane, oxazocane, and thiazocane.

In the specification, unless otherwise indicated, examples of aromatic heterocyclic rings include 5- or 6-membered aromatic heterocyclic rings. Specific examples include furan, thiophene, pyrrole, oxazole, isoxazole, thiazole, isothiazole, imidazole, pyrazole, 1,2,3-oxadiazole, 1,2,4-oxadiazole, 1,3,4-oxadiazole, furazan, 1,2,3-thiadiazole, 1,2,4-thiadiazole, 1,3,4-thiadiazole, 1,2,3-triazole, 1,2,4-triazole, tetrazole, pyridine, pyridazine, pyrimidine, pyrazine, and triazine.

Production Method

The production method according to the present disclosure is a method for producing a compound represented by formula (1):

(1)

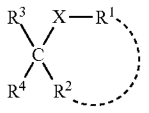

wherein

X represents —O—, an optionally substituted imino group, or —S—, $R^1$ represents a hydrogen atom or a hydrocarbyl group optionally having at least one substituent, and $R^2$ represents a hydrogen atom or a monovalent organic group, or $R^1$ and $R^2$, together with X and one carbon atom respectively adjacent to $R^1$ and $R^2$, may form a heterocyclic ring optionally having at least one substituent, $R^3$ represents a hydrogen atom or a monovalent organic group, and $R^4$ represents —$CF_2CH_3$ or —$CH_2CHF_2$; and the method includes step A of reacting a compound represented by formula (2):

(2)

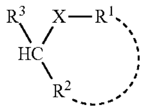

wherein the alphabetical symbols are as defined above with vinylidene fluoride under light irradiation.

In the specification, the compound represented by formula (1) may be referred to as "the compound of formula (1)" or "compound (1)."

In the specification, the compound represented by formula (2) may be referred to as "the compound of formula (2)" or "compound (2)."

X is preferably —O—.

$R^1$ is preferably a hydrogen atom, an alkyl group optionally having at least one substituent, or an aryl group optionally having at least one substituent.

$R^1$ is preferably a hydrogen atom, or an alkyl or aryl group optionally having at least one substituent selected from the group consisting of a ketone group, a nitrile group, a nitro group, a halogen group, an aryl group, —$SO_2R$, —SOR, —OP(═O) $(OR)_2$, and —OR; and R, in each occurrence, may be the same or different and represent a hydrogen atom or an alkyl group.

$R^2$ is preferably a hydrogen atom, an alkyl group optionally having at least one substituent, or an aryl group optionally having at least one substituent.

$R^2$ is preferably a hydrogen atom, or an alkyl or aryl group optionally having at least one substituent selected from the group consisting of a ketone group, a nitrile group, a nitro group, a halogen group, an aryl group, —$SO_2R$, —SOR, —OP(═O) $(OR)_2$, and —OR; and R, in each occurrence, may be the same or different and represent a hydrogen atom or an alkyl group.

$R^1$ and $R^2$, together with X and one carbon atom respectively adjacent to $R^1$ and $R^2$, preferably form a heterocyclic ring optionally having at least one substituent.

Here, X is preferably —O—; specifically, the heterocyclic ring is preferably an oxygen-containing heterocyclic ring. This ring is preferably a 5- or 6-membered ring.

Preferable examples of substituents of the heterocyclic ring include an alkyl group, an aryl group, a heteroaryl group, a ketone group, a nitrile group, a nitro group, a halogen group, —$SO_2R$, —SOR, —OP(═O) $(OR)_2$, and —OR.

$R^3$ is preferably a hydrogen atom, a hydrocarbyl group, or a hydrocarbyloxy group.

$R^3$ is more preferably a hydrogen atom, C1-C6 hydrocarbyl group, or a C1-C6 hydrocarbyloxy group.

$R^4$ is preferably —$CF_2CH_3$ or —$CH_2CHF_2$.

Preferably,

X is —O—;

$R^1$ is a hydrogen atom, an alkyl group optionally having at least one substituent (preferably a C1-C6 alkyl group), or an aryl group optionally having at least one substituent (preferably a C6-C10 aryl group) (preferably, a hydrogen atom, or an alkyl group (preferably C1-C6 alkyl group) or aryl group (preferably C6-C10 aryl group) optionally having at least one substituent selected from the group consisting of a ketone group, a nitrile group, a nitro group, a halogen group, an aryl group, —$SO_2R$, —SOR, —OP(═O) $(OR)_2$, and —OR; and R, in each occurrence, may be the same or different and represent a hydrogen atom or an alkyl group (preferably a C1-C6 alkyl group));

$R^2$ is a hydrogen atom, an alkyl group optionally having at least one substituent (preferably a C1-C6 alkyl group), or an aryl group optionally having at least one substituent (preferably, a hydrogen atom or an alkyl group (preferably a C1-C6 alkyl group) or aryl group (preferably a C6-C10 aryl group) optionally having at least one substituent selected from the group consisting of a ketone group, a nitrile group, a nitro group, a halogen group, an aryl group (preferably a C6-C10 aryl group), —$SO_2R$, —SOR, —OP(═O) $(OR)_2$, and —OR, and R, in each occurrence, may be the same or different and represents a hydrogen atom or an alkyl group (preferably a C1-C6 alkyl group), more preferably a hydrogen atom, or an alkyl group (preferably a C1-C6 alkyl group) or aryl group (preferably a C6-C10 aryl group) optionally having at least one substituent selected from the group consisting of a ketone group, a nitrile group, a nitro group, a halogen group, an aryl group, —$SO_2R$, —SOR, —OP(═O) $(OR)_2$, and —OR, and R, in each occurrence, may be the same or different and represents a hydrogen atom or an alkyl group (preferably a C1-C6 alkyl group)), or $R^1$ and $R^2$, together with X and one carbon atom respectively adjacent to $R^1$ and $R^2$, preferably form a heterocyclic ring optionally having at least one substituent;

$R^3$ is a hydrogen atom or a monovalent organic group (preferably a hydrogen atom, a hydrocarbyl group, or a hydrocarbyloxy; and more preferably a hydrogen atom, a C1-C10 hydrocarbyl group, or a C1-C10 hydrocarbyloxy); and $R^4$ is —$CF_2CH_3$ or —$CH_2CHF_2$.

Preferable examples of compound (2) include dioxolane (e.g., 1,3-dioxolane), methyl orthoformate, and ethyl orthoformate.

Step A

The reaction of step A can be performed, for example, by bringing a gas containing vinylidene fluoride into contact with a liquid containing compound (2).

A high content of vinylidene fluoride in the gas is preferable; specifically, for example, 80 v/v % or more, 90 v/v % or more, 95 v/v % or more, 98 v/v % or more, or 99 v/v % or more.

The contact can be preferably performed, for example, by introducing fine bubbles containing vinylidene fluoride into a liquid containing compound (1).

A high content of vinylidene fluoride in the fine bubbles is preferable; specifically, for example, 80 v/v % or more, 90 v/v % or more, 95 v/v % or more, 98 v/v % or more, or 99 v/v % or more.

Preferably, at least a portion of vinylidene fluoride, in the form of fine bubbles of gas containing vinylidene fluoride, is introduced into the liquid containing compound (2).

The liquid (i.e., the liquid medium in step A) is preferably a poor solvent of vinylidene fluoride.

The liquid medium can be a liquid medium containing at least one member selected from the group consisting of water and organic solvents that are poor solvents of vinylidene fluoride.

Specific examples of the liquid medium include water; alcohol solvents, such as methanol, ethanol, n-propanol, isopropyl alcohol, n-butanol, pentanol, hexanol, ethylene glycol, diethylene glycol, triethylene glycol, tetraethylene glycol, polyethylene glycol, propylene glycol, dipropylene glycol, tripropylene glycol, polypropylene glycol, trimethylene glycol, and hexanetriol; non-aromatic hydrocarbon solvents, such as pentane, hexane, heptane, octane, cyclohexane, decahydronaphthalene, n-decane, isododecane, and tridecane; aromatic hydrocarbon solvents, such as benzene, toluene, xylene, tetralin, veratrole, ethylbenzene, diethylbenzene, methylnaphthalene, anisole, phenetole nitrobenzene, o-nitrotoluene, mesitylene, indene, diphenyl sulfide, anisole, and propiophenone; ketone solvents, such as acetone, methyl ethyl ketone, diethyl ketone, hexanone, methyl isobutyl ketone, heptanone, diisobutyl ketone, acetonylacetone, methylhexanone, acetophenone, cyclohexanone, diacetone alcohol, propiophenone, and isophorone; halogenated hydrocarbon solvents, such as dichloromethane, chloroform, and chlorobenzene; ether solvents, such as diethyl ether, tetrahydrofuran (THF), diisopropyl ether, methyl-t-butyl ether (MTBE), dioxane, dimethoxyethane, diglyme, anisole, phenetole, 1,1-dimethoxy cyclohexane, diisoamyl ether, cyclopentyl methyl ether (CPME), dioxolane, methyl orthoformate, and ethyl orthoformate; ester solvents, such as ethyl acetate, isopropyl acetate, diethyl malonate, 3-methoxy-3-methylbutyl acetate, γ-butyrolactone, ethylene carbonate, propylene carbonate, dimethyl carbonate, and α-acetyl-γ-butyrolactone; nitrile solvents, such as acetonitrile, and benzonitrile; sulfoxide solvents, such as dimethyl sulfoxide, and sulfolane; amide solvents, such as N,N-dimethylformamide (DMF), N,N-dimethylacetamide, N-methylpyrrolidone (NMP), 1,3-dimethyl-2-imidazolidinone (DMI), N,N-dimethylacrylamide, N,N-dimethylacetoacetamide (DMA), N,N-diethylformamide, and N,N-diethylacetamide; and combinations of two or more of these substances.

Some or all of the reaction substrate in step A may function as the liquid medium. In the same manner, some or all of the liquid medium may function as the reaction substrate.

The percentage of vinylidene fluoride introduced in the form of fine bubbles of the entire vinylidene fluoride introduced into the liquid is preferably higher.

The fine bubbles can be formed by a commonly used method. Examples of such methods include the following:

(a) a method using supersaturation (specifically, a method in which solute gas is pressurized in a closed container containing a solvent to dissolve a sufficient amount of the solute gas, and then the solvent in which the solute gas is dissolved by pressurization is decompressed to generate microbubbles of the solute gas in the solvent); and (b) a gas-liquid shear method (i.e., a method in which solute gas is supplied to a vortex flow of a solvent, and the solute gas is sheared in the solvent to generate fine bubbles of the solute gas in the solvent).

The fine bubbles in the method according to the present disclosure can be formed by using either method above with a fine bubble generator.

For example, the fine bubble generator may have the function of creating fine bubbles in a liquid by injecting a gas into a liquid, and repeatedly dividing the liquid by applying a shearing force to the flow of the mixture of the gas and liquid with a static mixer.

Examples of methods for generating fine bubbles include a pressurized dissolution method, a swirling flow method, a method using a static mixer, a cavitation method, and a Venturi method.

The amount of vinylidene fluoride gas supplied (or the rate of supply) to the reaction system in step A can be determined in consideration of the size of the reaction vessel, the permeability of light, and the capability of the bubble generator.

Specifically, vinylidene fluoride can be supplied, for example, in an amount of typically 1 to 99 vol %, preferably 5 to 80 vol %, and more preferably 10 to 50 vol %, per minute, based on the volume of the reaction solution in the reaction system.

The fine bubbles are preferably ultrafine bubbles. In the specification, "ultrafine bubbles" refers to bubbles with a diameter of 1 μm or less, according to the definition from the International Organization for Standardization (ISO).

Ultrafine bubbles can be prepared by using a commercially available equipment (e.g., SMX554, SMX374, SKA115T, SMX115, ASG1, ASG2, MA3FS, MA3, MASS, BA06S, and AMB3, all from HACK UFB Co., Ltd; and FBG-OS Type 1, from PMS).

Suitable forms of the fine bubbles are the following: preferably, the percentage of the number of bubbles having a particle size within the range of 10 nm to 1 μm is 90% or more of the total number of bubbles in the gas; more preferably the percentage of the number of bubbles having a particle size within the range of 50 nm to 1 μm is 90% or more of the total number of bubbles in the gas; and the percentage of the number of bubbles having a particle size within the range of 50 nm to 500 nm is 90% or more of the total number of bubbles in the gas.

The particle size and the number of fine bubbles, as well as their distribution and the mean particle size, are measured by nanoparticle tracking analysis, which is a method for measuring the Brownian-diffusion-equivalent diameter using laser beams on a number basis. The measurement can be performed with the commercially available instrument NanoSight LM-10 (NanoSight Ltd.), or equipment equivalent thereto.

However, if the measurement cannot be accurately performed by the nanoparticle tracking analysis, another method may be used. Such alternative methods include the following:

(1) A method using a Particle Sensor PS100 (trade name, Hokuto Electronics, Inc.) or an equivalent thereto as a method for measuring the diameter of nanobubbles;

(2) A method using a SALD-7100 Shimadzu Nanoparticle Size Distribution Analyzer (trade name, Shimadzu Corporation) or an equivalent thereto as a method for measuring both the diameter of microbubbles and the diameter of nanobubbles; and (3) A method that combines these measurement methods.

The ratio of the volume of the gas containing vinylidene fluoride to the volume of the liquid containing compound (2) in the reaction system of step A is typically within the range of 0.01 to 1; preferably within the range of 0.02 to 0.9; more preferably within the range of 0.05 to 0.8; and still more preferably within the range of 0.1 to 0.5.

The reaction in step A is performed under light irradiation. For example, the irradiation light for use in the light irradiation can be any light that can initiate and/or facilitate the reaction in step A. Examples of light sources include low-, medium-, or high-pressure mercury lamps, tungsten lamps, and light-emitting diodes (LEDs).

The irradiated light is preferably light containing ultraviolet light. The initiation of light irradiation can be before, during, at the same time as, or after the mixing operation. It is sufficient if the intensity of light irradiation can supply energy that can initiate and/or facilitate the reaction in step A. The intensity of light irradiation can be suitably adjusted, for example, by adjusting the output of the light source and the distance between the light source and the reaction system of step A based on common technical knowledge, so that the reaction in step A proceeds appropriately.

The lower limit of the reaction temperature in step A can be preferably −50° C., more preferably −10° C., still more preferably 0° C., yet more preferably 10° C., and particularly preferably 20° C. The upper limit of the reaction temperature in step A can be preferably 130° C., more preferably 100° C., still more preferably 80° C., yet more preferably 50° C., and particularly preferably 30° C. The reaction temperature in step A can be within the range of preferably −10 to 130° C., more preferably 0 to 100° C., still more preferably 10 to 80° C., particularly preferably 10 to 50° C., and particularly more preferably 10 to 30° C.

The reaction in step A can be suitably performed at room temperature. An overly high reaction temperature may be disadvantageous in terms of cost, and may cause an undesirable reaction. The lower the upper limit of the reaction temperature in step A, the more likely side reactions are suppressed. The higher the lower limit of the reaction temperature in step A, the more likely the progress of the target reaction accelerates.

The lower limit of the amount of vinylidene fluoride per mol of compound (2) in the reaction of step A can be preferably 0.001 mol, more preferably 0.002 mol, and still more preferably 0.003 mol. The upper limit of the amount of vinylidene fluoride per mol of compound (2) in the reaction of step A can be preferably 10 mol, more preferably 5 mol, and still more preferably 3 mol. The amount of vinylidene fluoride per mol of compound (2) can be within the range of preferably 0.001 to 10 mol, more preferably 0.002 to 5 mol, and still more preferably 0.003 to 3 mol. The target product can be efficiently obtained by performing the reaction with vinylidene fluoride in an amount within these ranges.

The light in step A preferably contains UV light. The UV light preferably has a dominant wavelength within the range of 200 nm to 400 nm, and more preferably 220 nm to 350 nm. The light in step A may contain light other than UV light. The light irradiation may be performed, for example, by using a mercury lamp (e.g., a low-pressure mercury lamp, a medium-pressure mercury lamp, and a high-pressure mercury lamp), a UV-LED, an excimer lamp, or a combination of these lamps.

The light preferably reaches at least a portion of the reaction system in step A with a light irradiation density of preferably 0.01 $W/m^2$ or more, more preferably 0.1 $W/m^2$ or more, still more preferably 1 $W/m^2$ or more, and yet more preferably 10 $W/m^2$ or more. The upper limit of the light irradiation density can be, for example, 1000 $W/m^2$, 700 $W/m^2$, or 500 W/m. The light irradiation density can be within the range of, for example, 0.01 $W/m^2$ to 1000 W/m, 0.1 W/m to 700 $W/m^2$, or 1 $W/m^2$ to 500 $W/m^2$.

The lower limit of the reaction time in step A can be preferably 0.5 hours, more preferably 1 hour, and still more preferably 1.5 hours. The upper limit of the reaction time in step A can be preferably 72 hours, more preferably 48 hours, and still more preferably 24 hours. The reaction time in step A can be within the range of preferably 0.5 to 72 hours, more preferably 1 to 48 hours, and still more preferably 1.5 to 24 hours. An overly short reaction time may result in an insufficient reaction in step A. An overly long reaction time is disadvantageous in terms of cost, and may cause an undesirable reaction.

The reaction can be performed in the presence or absence of an inert gas (e.g., nitrogen gas). The inert gas may be introduced into the reaction system of step A, together with vinylidene fluoride.

The reaction in step A can be preferably performed in the presence of at least one member selected from the group consisting of reaction initiators (e.g., radical reaction initiators) and photosensitizers. Examples of reaction initiators (e.g., radical reaction initiators) include α-diketone compounds (e.g., benzyl, and diacetyl), acyloin compounds (e.g., benzoin), acyloin ether compounds (e.g., benzoin methyl ether, benzoin ethyl ether, and benzoin isopropyl ether), thioxanthone compounds (e.g., thioxanthone, 2,4-diethyl thioxanthone, and thioxanthone-4-sulfonic acid), acetophenone compounds (e.g., acetophenone, 2-(4-toluenesulfonyloxy)-2-phenylacetophenone, p-dimethylaminoacetophenone, 2,2'-dimethoxy-2-phenylacetophenone, p-methoxyacetophenone, 2-methyl [4-(methylthio)phenyl]-2-morpholino-1-propanone, and 2-benzyl-2-dimethylamino-1-(4-morpholinophenyl)-butan-1-one), aminobenzoic acid compounds (e.g., ethyl 2-dimethylaminobenzoate, ethyl 4-dimethylaminobenzoate, (n-butoxy)ethyl 4-dimethylaminobenzoate, isoamyl 4-dimethylaminobenzoate, and 2-ethylhexyl 4-dimethylamino benzoate), halogenated compounds (e.g., phenacyl chloride, and trihalomethylphenylsulfone), acylphosphine oxide compounds, peroxides (e.g., di-t-butyl peroxide), and alkylphenone compounds (e.g., Irgacure 127, trade name, Merck & Co., Inc.). The amount of the reaction initiator for use can be within the range of preferably 0.00001 to 10 mol, more preferably 0.0001 to 1 mol, and still more preferably 0.001 to 0.1 mol, per 100 mol of vinylidene fluoride.

Examples of photosensitizers include ketone compounds (e.g., acetone), benzophenone compounds (e.g., benzophenone, 4,4'-bis(dimethylamino) benzophenone, and 4,4'-bis (diethylamino) benzophenone), anthracene compounds (e.g., anthracene), quinone compounds (e.g., anthraquinone, and 1,4-naphthoquinone), thiopyrillium salt compounds, merocyanine compounds, quinoline compounds, styryl compounds, coumarin compounds, ketocoumarin compounds, thioxanthene compounds, xanthene compounds, oxonol compounds, cyanine compounds, rhodamine compounds, and pyrylium salt compounds. These photosensitizers can be used singly, or in a combination of two or more.

Typically, a styryl compound, a quinoline compound, or a coumarin compound is preferable. Specific examples of styryl compounds or quinoline compounds include 2-(p-dimethylaminostyryl) quinoline, 2-(p-diethylaminostyryl) quinoline, 4-(p-dimethylaminostyryl) quinoline, 4-(p-diethylaminostyryl) quinoline, 2-(p-dimethylaminostyryl)-3,3-3H-indole, 2-(p-diethylaminostyryl)-3,3-3H-indole, 2-(p-dimethylaminostyryl) benzoxazole, 2-(p-diethylaminostyryl) benzoxazole, 2-(p-dimethylaminostyryl) benzimidazole, and 2-(p-diethylaminostyryl) benzimidazole.

Specific examples of courarin compounds include 7-diethylamino-4-methylcoumarin, 7-ethylamino-4-trifluoromethylcoumarin, 4,6-diethylamino-7-ethylaminocoumarin, 3-(2-benzimidazolyl)-7-N,N-diethylaminocoumarin, 7-diethylaminocyclopenta(c)coumarin, 7-amino-4-trifluoromethylcoumarin, 1,2,3,4,5,3H,6H,10H-tetrahydro-8-trifluoromethyl(1)benzopyrano-(9,9A,1-gh)-quinolizin-10-one, 7-ethylamino-6-methyl-4-trifluoromethylcoumarin, and 1,2,3,4,5,3H,6H,10H-tetrahydro-9-carbethoxy(1) benzopyrano (9,9a,1-gh)-quinolizin-10.

In the production method according to the present disclosure, the starting material conversion rate can be preferably 10% or more, more preferably 30% or more, and still more preferably 50% or more.

In the production method according to the present disclosure, the selectivity for the target compound can be preferably 80% or more, and more preferably 90, or more.

In the production method according to the present disclosure, the yield of the target compound can be preferably 50% or more, and more preferably 70, or more.

Compound

The compound according to the present disclosure is a compound represented by formula (1):

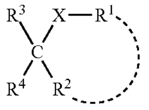

(1)

wherein

X represents —O—, an optionally substituted imino group, or —S—, $R^1$ represents a hydrogen atom or a hydrocarbyl group optionally having at least one substituent, and $R^2$ represents a hydrogen atom or a monovalent organic group, or $R^1$ and $R^2$, together with X and one carbon atom respectively adjacent to $R^1$ and $R^2$, may form a heterocyclic ring optionally having at least one substituent, $R^3$ represents a hydrogen atom or a monovalent organic group, and $R^4$ represents $—CF_2CH_3$ or $—CH_2CHF_2$, with the proviso that 3,3-difluoro-2-methyl-2-butanol and 4,4-difluoro-2-methyl-2-butanol are excluded.

Preferable embodiments of the compound can be understood based on the description of the compound in the section "Production Method."

Composition

The vinylidene-fluoride-containing composition according to the present disclosure contains (1) vinylidene fluoride, and (2) a liquid medium that is a poor solvent of vinylidene fluoride, wherein at least a portion of the vinylidene fluoride is in a form of fine bubbles of gas and is dispersed in the liquid medium.

The liquid medium preferably contains at least one member selected from the group consisting of water and organic solvents that are poor solvents of vinylidene fluoride.

Most of the vinylidene fluoride, other than the vinylidene fluoride dissolved in the poor solvent, is preferably dispersed in a form of fine bubbles.

The fine bubbles are in such a form that the percentage of the number of bubbles having a particle size within a range of 5 nm to 100 μm is 90- or more of the total number of bubbles of the gas.

The ratio of the volume of the gas containing vinylidene fluoride to the volume of the liquid containing the compound represented by formula (2) in the composition is typically within a range of 0.01 to 1, preferably 0.02 to 0.9, more preferably 0.05 to 0.8, and still more preferably 0.1 to 0.5.

The average dispersed particle size can be preferably 10 μm or less, more preferably 5 μm or less, still more preferably 1 μm or less, even more preferably 500 nm or less, and particularly preferably 300 nm or less.

The average dispersed particle size can be, for example, 5 nm or more, 10 nm or more, 50 nm or more, or 100 nm or more.

The composition may be placed in a sealable container (e.g., a cylinder). The present disclosure also provides a sealable container (e.g., a cylinder) in which the composition is enclosed.

The forms of the bubbles are the following: preferably, the percentage of the number of bubbles having a particle size within the range of 10 nm to 1 μm is 90% or more of the total number of bubbles of the gas; more preferably the percentage of the number of bubbles having a particle size within the range of 50 nm to 1 μm is 90% or more of the total number of bubbles of the gas; and the percentage of the number of bubbles having a particle size within the range of 50 nm to 500 nm is 90% or more of the total number of bubbles of the gas.

The details of the composition can be understood based on the description in the section "Production Method."

The liquid medium preferably contains at least one member selected from the group consisting of water and organic solvents that are poor solvents of vinylidene fluoride.

The method for producing the composition can be understood based on the method for generating fine bubbles described in the section "Production Method."

The fine bubbles are preferably in such a manner that the percentage of the number of bubbles having a particle size within the range of 5 nm to 100 μm is 90% or more of the total number of bubbles of the gas.

A form other than this form, or a more preferable form, can be understood based on other parts of the present disclosure.

Composition Containing a Fluorine-Containing Olefin

The present disclosure also provides the following composition containing a fluorine-containing olefin. The composition containing a fluorine-containing olefin contains (1) a fluorine-containing olefin, which however excludes vinylidene fluoride, and (2) a liquid medium, wherein at least a portion of the fluorine-containing olefin is in a form of fine bubbles of gas and is dispersed in the liquid medium.

The fluorine-containing olefin is preferably a compound represented by formula (3):

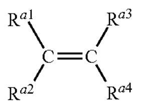

(3)

wherein $R^{a1}$, $R^{a2}$, $R^{a3}$, and $R^{a4}$ are the same or different and each represent a hydrogen atom, a fluorine atom, a chlorine atom, or a fluoroalkyl group, with the proviso that of $R^{a1}$, $R^{a2}$, $R^{a3}$, and $R^{a4}$, at least one is a fluorine atom.

Specific examples include tetrafluoroethylene, chlorotrifluoroethylene, and hexafluoropropene.

The liquid medium preferably contains at least one member selected from the group consisting of water and organic solvents that are poor solvents of the fluorine-containing olefin represented by formula (3), which, however, exclude vinylidene fluoride.

The fine bubbles are preferably in such a manner that the percentage of the number of bubbles having a particle size within the range of 5 nm to 100 μm is 90% or more of the total number of bubbles of the gas.

The embodiments of the composition containing a fluorine-containing olefin (however, excluding vinylidene fluoride) can be understood by a person skilled in the art with reference to the description of the vinylidene-fluoride-containing composition.

The fine bubbles of the composition can be formed by a commonly used method. Examples of such methods include (1) a method using supersaturation in which solute gas is pressurized in a closed container containing a solvent to dissolve a sufficient amount of the solute gas, and then the solvent in which the solute gas is dissolved by pressurization is decompressed to generate microbubbles of the solute gas in the solvent.

Another method is a gas-liquid shear method (i.e., a method in which solute gas is supplied to a vortex flow of a solvent, and the solute gas is sheared in the solvent to generate fine bubbles of the solute gas in the solvent). The fine bubbles of the composition can be formed by using either method above with a fine bubble or microbubble generator.

Nanobubble generators have the function of creating nanobubbles in a liquid by injecting a gas into a liquid, and repeatedly dividing the liquid by applying a shearing force to the flow of the mixture of the gas and liquid with a static mixer.

Examples of methods for generating microbubbles include a pressurized dissolution method, a swirling flow method, a method using a static mixer, a cavitation method, and a Venturi method.

The particle size and the number of fine bubbles, as well as their distribution and mean particle size, can be measured by the methods described above.

Although embodiments are described above, it can be understood that various changes of the embodiments and details are possible without departing from the principal concept and scope of the claims.

Item 1. A method for producing a compound represented by formula (1):

(1)

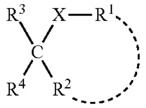

wherein

X represents —O—, an optionally substituted imino group, or —S—, $R^1$ represents a hydrogen atom or a hydrocarbyl group optionally having at least one substituent, and $R^2$ represents a hydrogen atom or a monovalent organic group, or $R^1$ and $R^2$, together with X and one carbon atom respectively adjacent to $R^1$ and $R^2$, may form a heterocyclic ring optionally having at least one substituent, $R^3$ represents a hydrogen atom or a monovalent organic group, and $R^4$ represents $—CF_2CH_3$ or $—CH_2CHF_2$;

the method comprising step A of reacting a compound represented by formula (2):

(2)

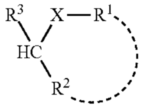

wherein alphabetical symbols are as defined above, with vinylidene fluoride under light irradiation.

Item 2. The production method according to Item 1, wherein X is —O—.

Item 3. The production method according to Item 1 or 2, wherein $R^1$ represents a hydrogen atom, an alkyl group optionally having at least one substituent, or an aryl group or heteroaryl group optionally having at least one substituent.

Item 4. The production method according to Item 3, wherein $R^1$ represents a hydrogen atom, or an alkyl or aryl group optionally having at least one substituent selected from the group consisting of a ketone group, a nitrile group, a nitro group, a halogen group, an aryl group, $—SO_2R$, —SOR, $—OP(=O)(OR)_2$, and —OR; and R, in each occurrence, may be the same or different and represents a hydrogen atom, an alkyl group, or an aryl group.

Item 5. The production method according to any one of Items 1 to 4, wherein $R^2$ represents a hydrogen atom, an alkyl group optionally having at least one substituent, or an aryl group optionally having at least one substituent.

Item 6. The production method according to Item 5, wherein $R^2$ represents a hydrogen atom, or an alkyl or aryl group optionally having at least one substituent selected from the group consisting of a ketone group, a nitrile group, a nitro group, a halogen group, an aryl group, $—SO_2R$, —SOR, $—OP(=O)(OR)_2$, and —OR; and R, in each occurrence, may be the same or different and represents a hydrogen atom, an alkyl group, or an aryl group.

Item 7. The production method according to any one of Items 1 to 6, wherein $R^1$ and $R^2$, together with X and one carbon atom respectively adjacent to $R^1$ and $R^2$, are in a form of a heterocyclic ring optionally having at least one substituent.

Item 8. The production method according to any one of Items 1 to 7, wherein $R^3$ represents a hydrogen atom, a hydrocarbyl group, or a hydrocarbyloxy group.

Item 9. The production method according to any one of Items 1 to 8, wherein $R^4$ represents $—CF_2CH_3$ or $—CH_2CHF_2$.

Item 10. The production method according to any one of Items 1 to 9, wherein at least a portion of the vinylidene fluoride is in a form of fine bubbles, and the fine bubbles containing the at least a portion of the vinylidene fluoride are introduced into a liquid containing the compound represented by formula (2).

Item 11. The production method according to Item 10, wherein the fine bubbles are in such a form that the percentage of the number of bubbles having a particle size within a range of 5 nm to 100 μm is 90% or more of the total number of the bubbles.

Item 12. The production method according to any one of Items 1 to 11, wherein the ratio of the volume of the gas containing vinylidene fluoride to the volume of a liquid containing the compound represented by formula (2) is within a range of 0.01 to 1.

Item 13. The production method according to any one of Items 1 to 12, wherein the reaction temperature in step A is 130° C. or less.

Item 14. The production method according to any one of Items 1 to 13, wherein the light in step A contains UV light.

Item 15 A compound represented by formula (1):

(1)

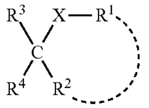

wherein

X represents —O—, an optionally substituted imino group, or —S—, $R^1$ represents a hydrogen atom or an hydrocarbyl group optionally having at least one substituent, and $R^2$ represents a hydrogen atom or a monovalent organic group, or $R^1$ and $R^2$, together with X and one carbon atom respectively adjacent to $R^1$ and $R^2$, may form a heterocyclic ring optionally having at least one substituent, $R^3$ represents a hydrogen atom or a monovalent organic group, and $R^4$ represents $—CF_2CH_3$ or $—CH_2CHF_2$, with the proviso that 3,3-difluoro-2-methyl-2-butanol and 4,4-difluoro-2-methyl-2-butanol are excluded.

Item 16. A vinylidene-fluoride-containing composition, the composition comprising (1) vinylidene fluoride, and (2) a liquid medium, wherein at least a portion of the vinylidene fluoride in a form of fine bubbles is dispersed in the liquid medium.

Item 17. The vinylidene-fluoride-containing composition according to Item 16, wherein the liquid medium contains at least one member selected from the group consisting of water and organic solvents that are poor solvents for vinylidene fluoride.

Item 18. The composition according to Item 16 or 17, wherein the fine bubbles are in such a form that the percentage of the number of bubbles having a particle size within a range of 5 nm to 100 μm is 90% or more of the total number of the bubbles.

Item 19. A composition containing a fluorine-containing olefin, the composition comprising (1) a fluorine-containing olefin, the fluorine-containing olefin excluding vinylidene fluoride, and (2) a liquid medium, wherein at least a portion of the fluorine-containing olefin in a form of fine bubbles is dispersed in the liquid medium.

Item 20. The composition containing a fluorine-containing olefin according to Item 19, wherein the fluorine-containing olefin is a compound represented by formula (3):

(3)

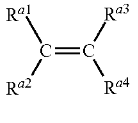

wherein $R^{a1}$, $R^{a2}$, $R^{a3}$, and $R^{a4}$ are the same or different and each represent a hydrogen atom, a fluorine atom, a chlorine atom, or a fluoroalkyl group, with the proviso that of $R^{a1}$, $R^{a2}$, $R^{a3}$, and $R^{a4}$, at least one is a fluorine atom.

Item 21. The composition containing a fluorine-containing olefin according to Item 19 or 20, wherein the liquid medium contains at least one member selected from the group consisting of water and organic solvents that are poor solvents for the fluorine-containing olefin represented by formula (3), with the proviso that the fluorine-containing olefin excludes vinylidene fluoride.

Item 22. The composition according to any one of Items 19 to 21, wherein the fine bubbles are in such a form that the percentage of the number of bubbles having a particle size within a range of 5 nm to 100 μm is 90% or more of the total number of the bubbles.

EXAMPLES

The following describes the aspects of the present disclosure in more detail, with reference to Examples. However, the aspects of the present disclosure are not limited to the Examples.

The meaning of the symbols and abbreviations used in the Examples is given below.

VdF: vinylidene fluoride

Examples 1 to 3

In Examples 1 to 3, the following compounds A to D were produced from VdF.

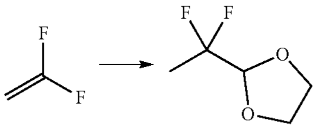

A

B

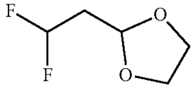

C

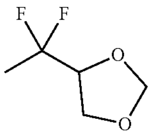

D

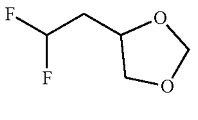

Figure 2:
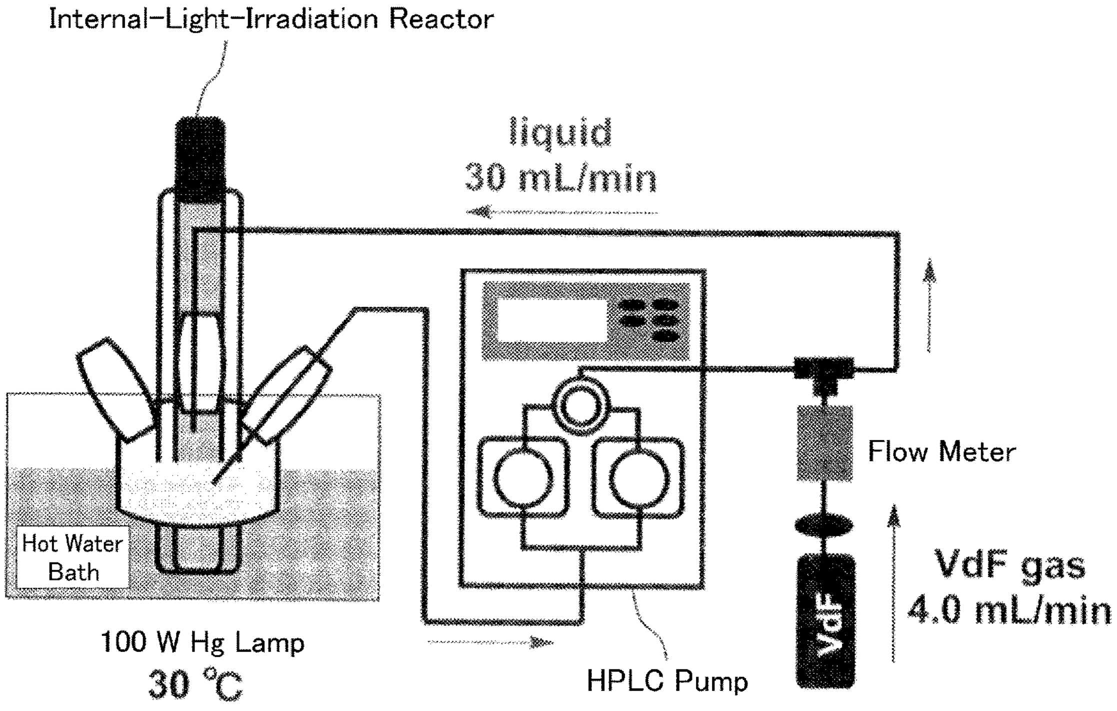
FIG. 2 shows an overview of another apparatus used in the production method according to the present disclosure (Example 10).
Figure 3:
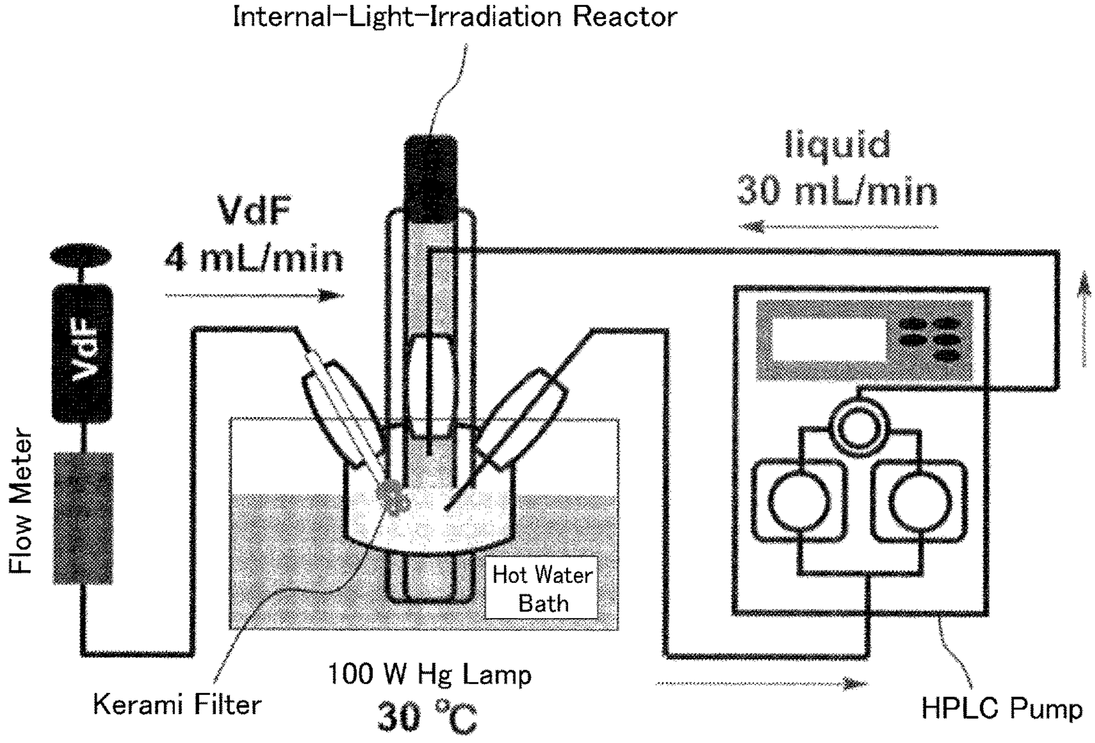
FIG. 3 shows an overview of another apparatus used in the production method according to the present disclosure (Example 11).
Figure 4:
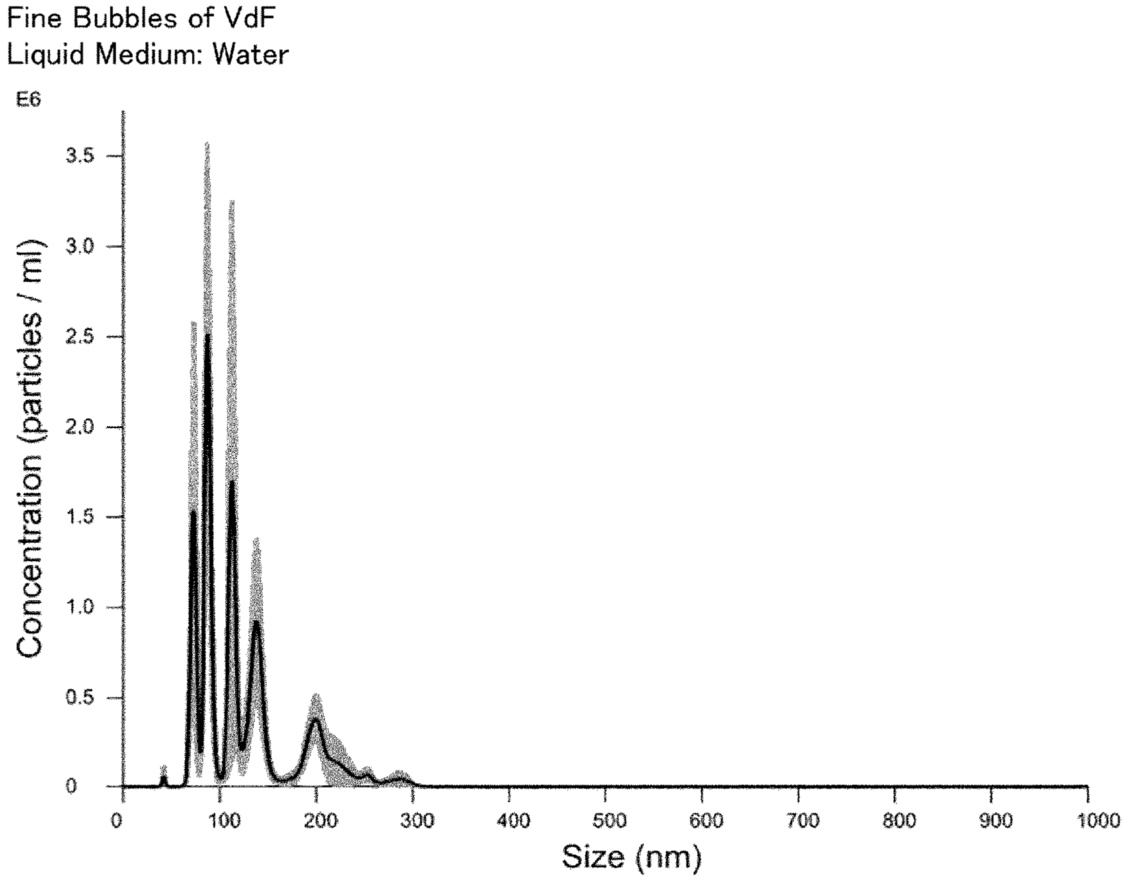
FIG. 4 is a graph showing the measurement results of the particle size and the number of fine bubbles of VdF in water as a liquid medium (Example 12).
Figure 5:
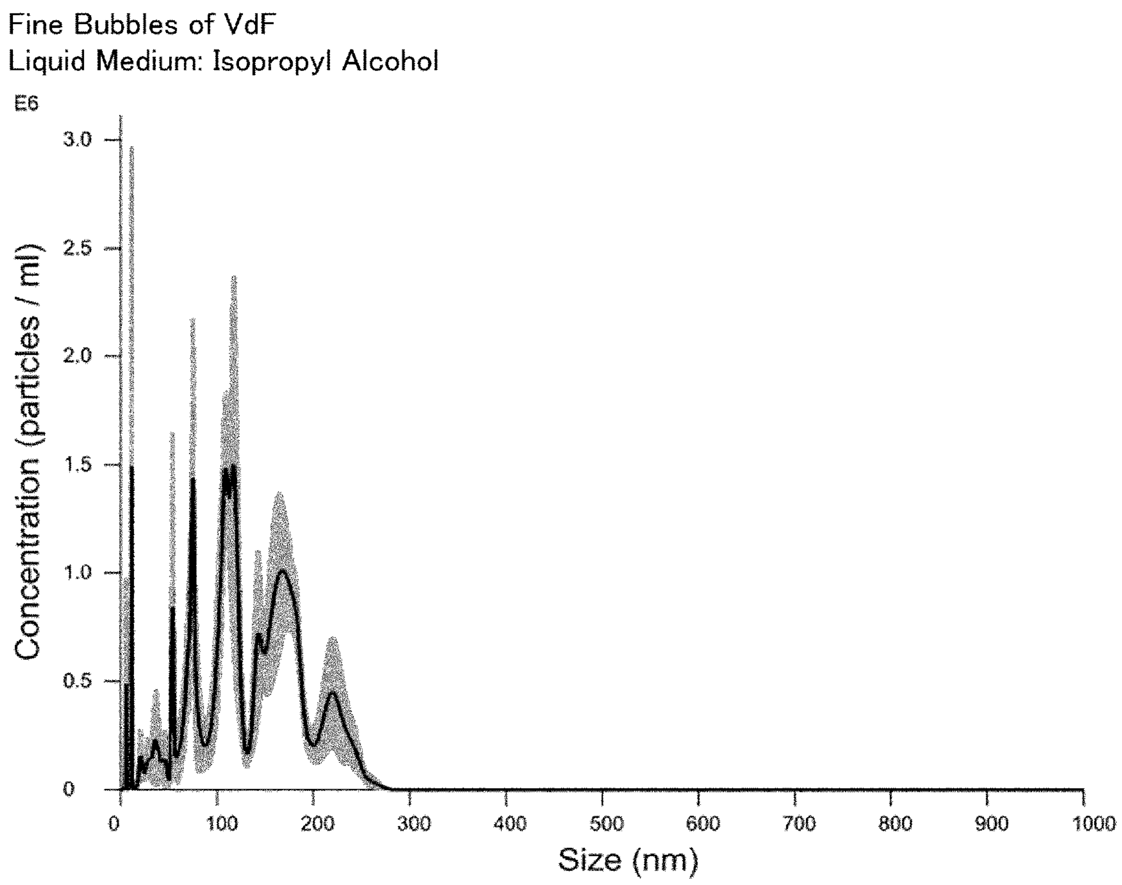
FIG. 5 is a graph showing the measurement results of the particle size and the number of fine bubbles of VdF in isopropyl alcohol as a liquid medium (Example 12)).
Figure 6:
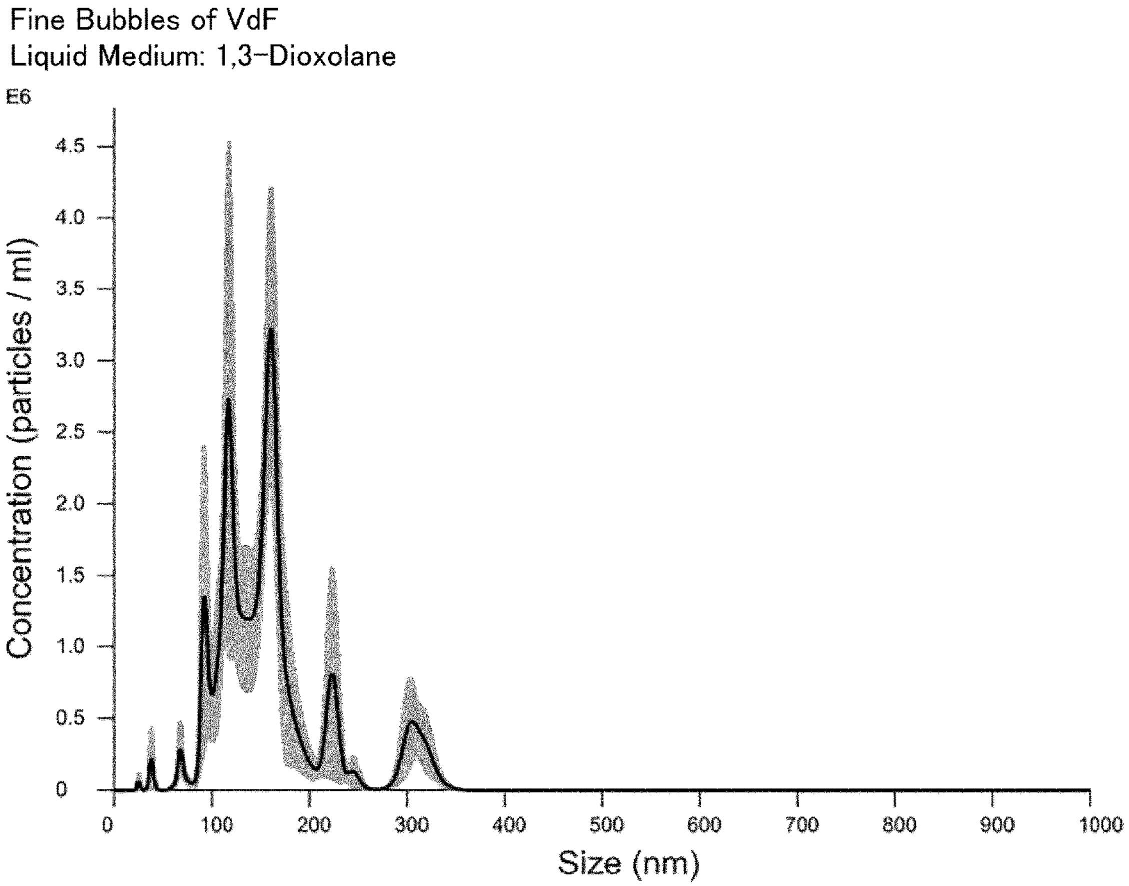
FIG. 6 is a graph showing the measurement results of the particle size and the number of fine bubbles of VdF in 1,3-dioxolane as a liquid medium (Example 12).
Figure 7:
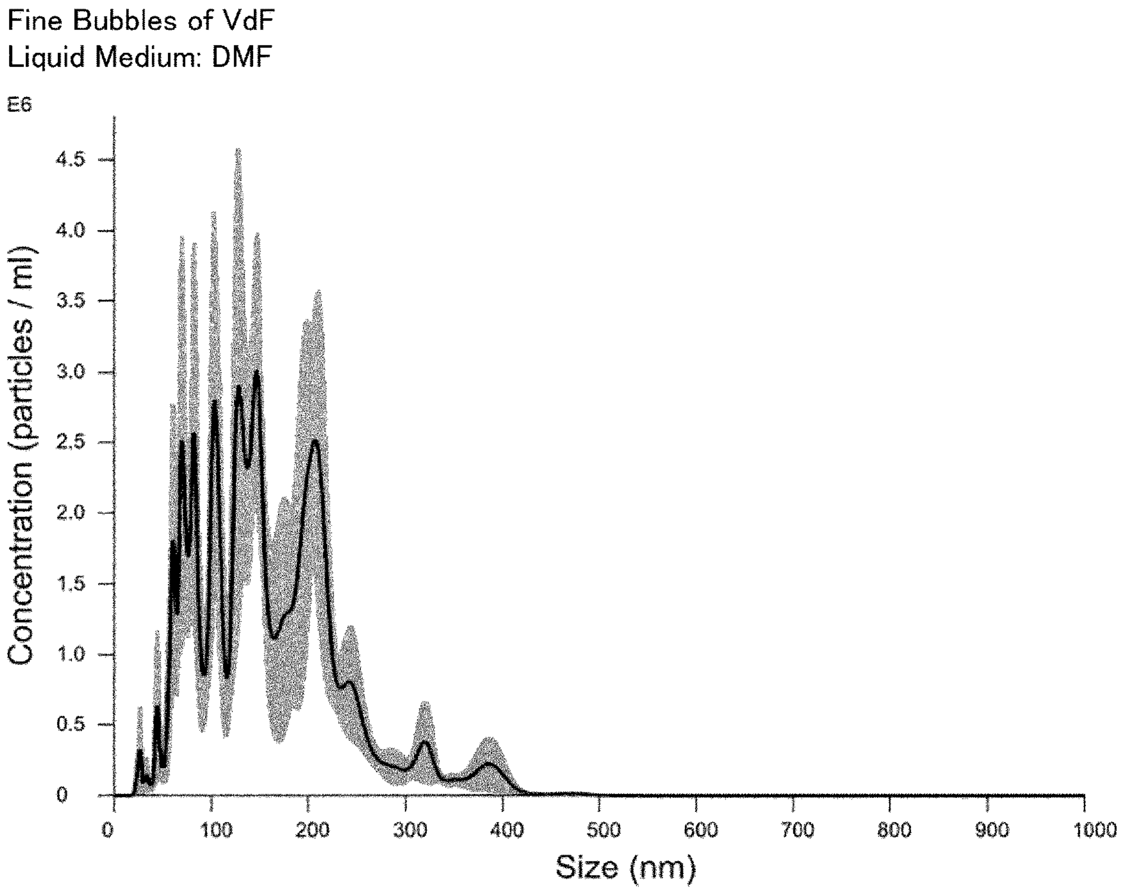
FIG. 7 is a graph showing the measurement results of the particle size and the number of fine bubbles of VdF in DMF as a liquid medium (Example 12).
Figure 8:
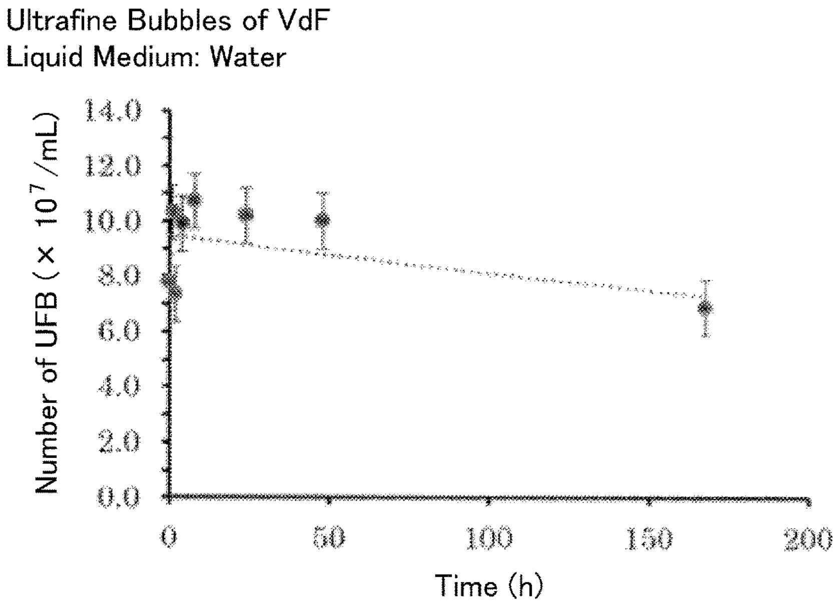
FIG. 8 is a graph showing a change over time in the number of ultrafine bubbles in water (Example 13).
Figure 9:
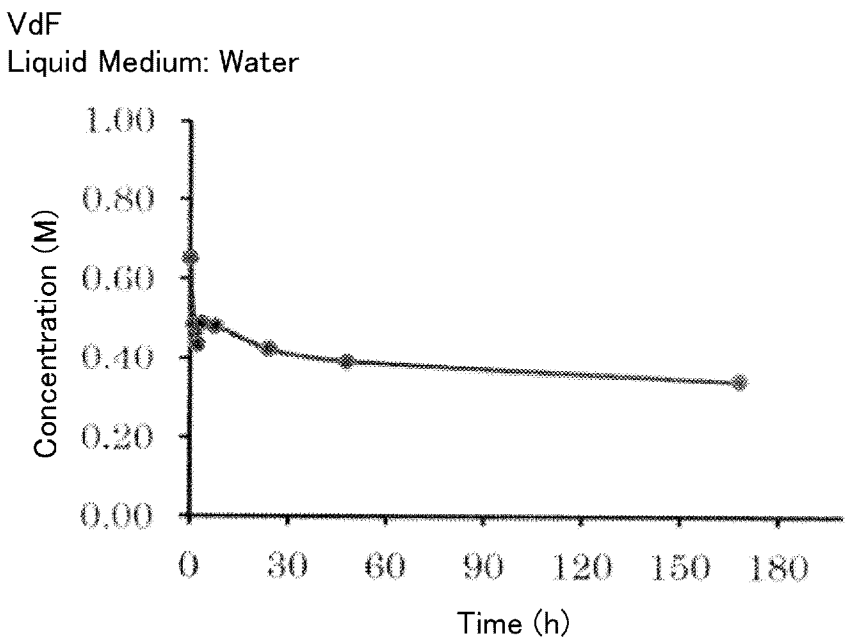
FIG. 9 is a graph showing a change over time in the concentration of VdF in water (Example 13).
Figure 10:
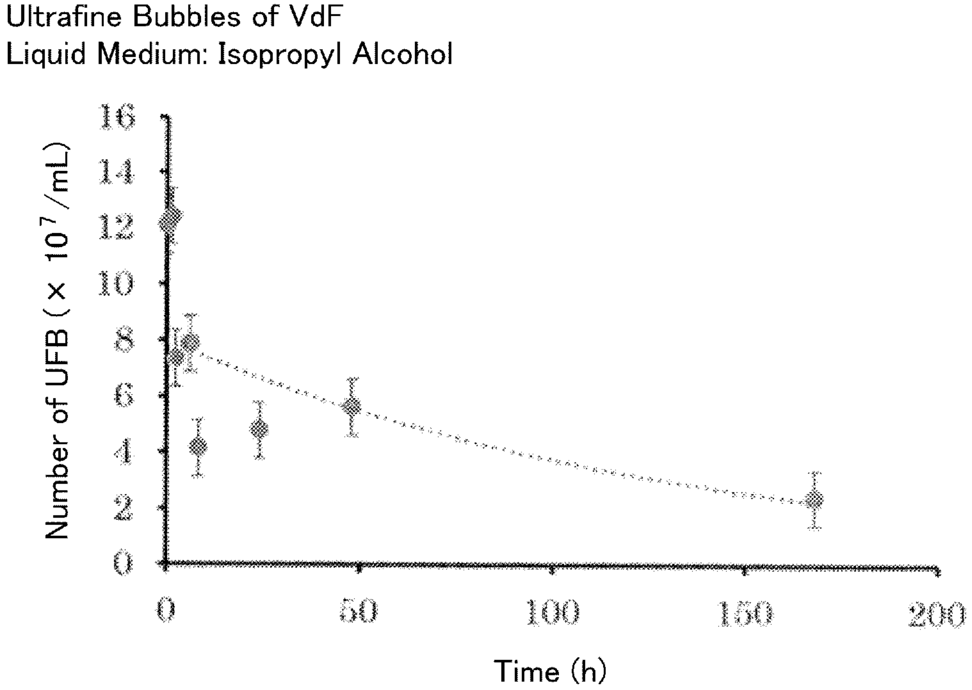
FIG. 10 is a graph showing a change over time in the number of ultrafine bubbles in isopropyl alcohol (Example 13).
Figure 11:
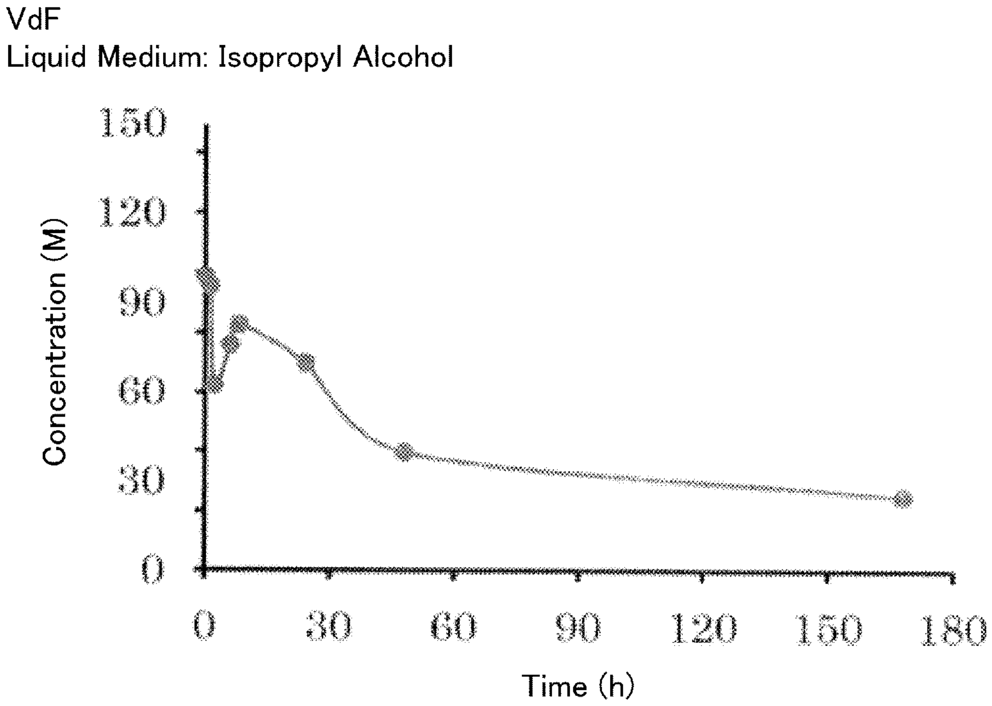
FIG. 11 is a graph showing a change over time in the concentration of VdF in isopropyl alcohol (Example 13).
Figure 12:
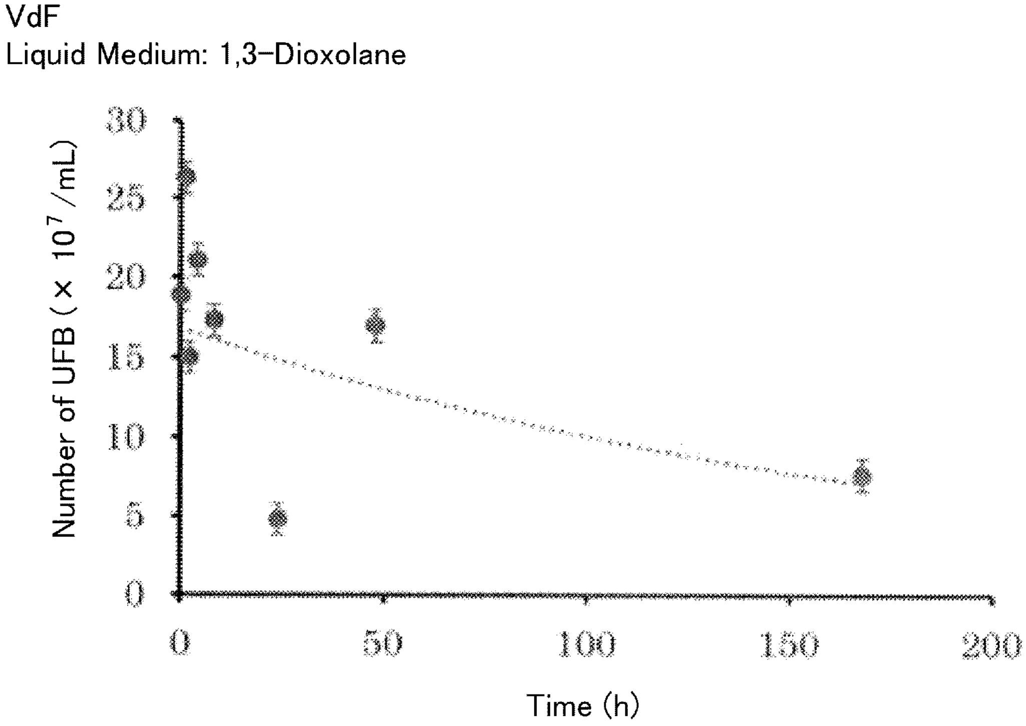
FIG. 12 is a graph showing a change over time in the number of ultrafine bubbles in 1,3-dioxolane (Example 13).
Figure 13:
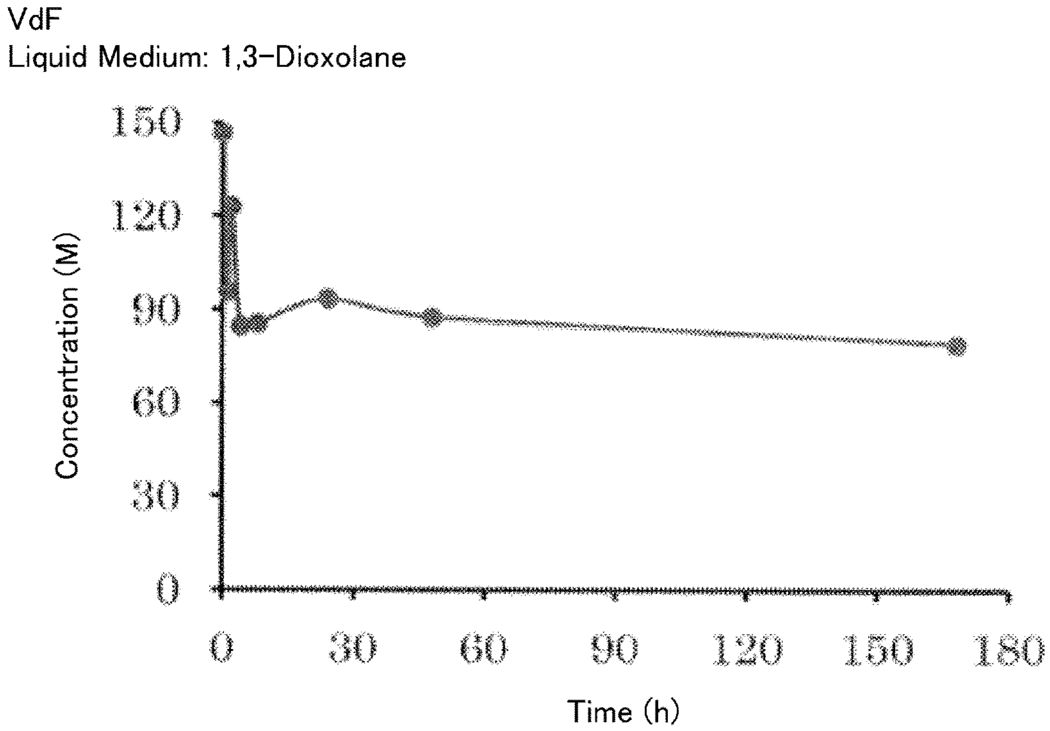
FIG. 13 is a graph showing a change over time in the concentration of VdF in 1,3-dioxolane (Example 13).
Figure 14:
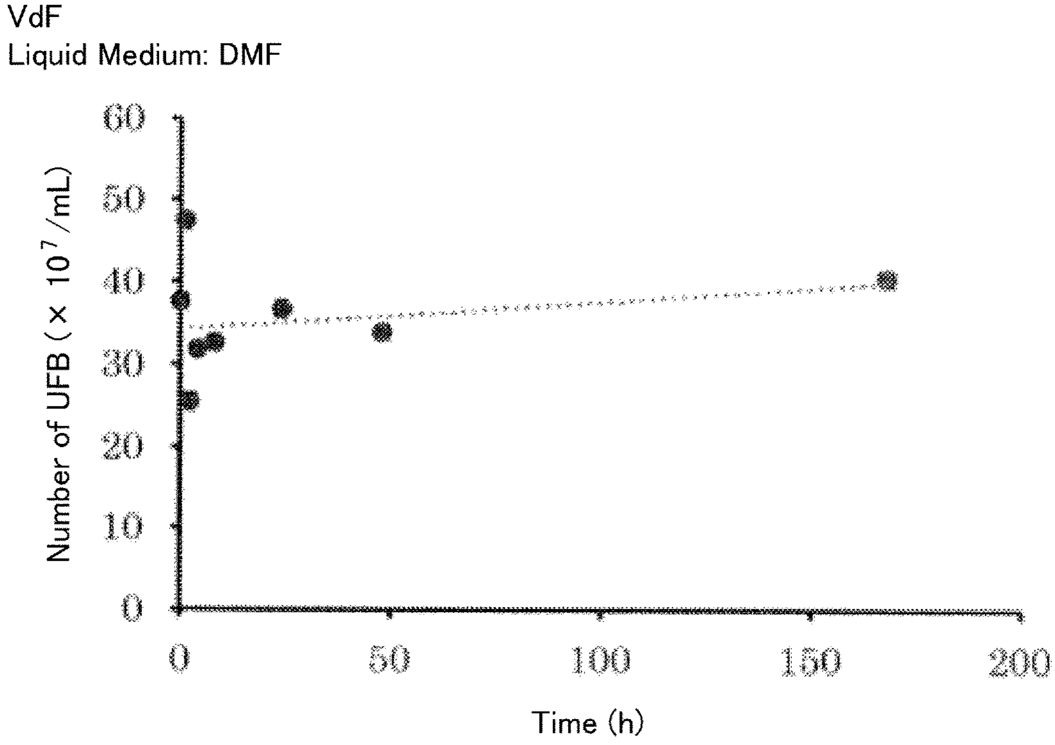
FIG. 14 is a graph showing a change over time in the number of ultrafine bubbles in DMF (Example 13).
Figure 15:
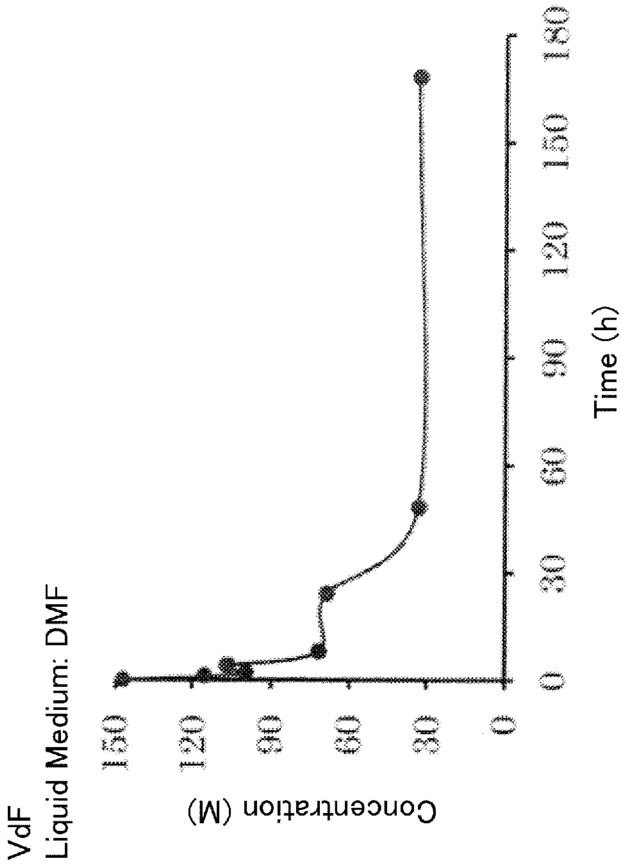
FIG. 15 is a graph showing a change over time in the concentration of VdF in DMF (Example 13).
Figure 16:
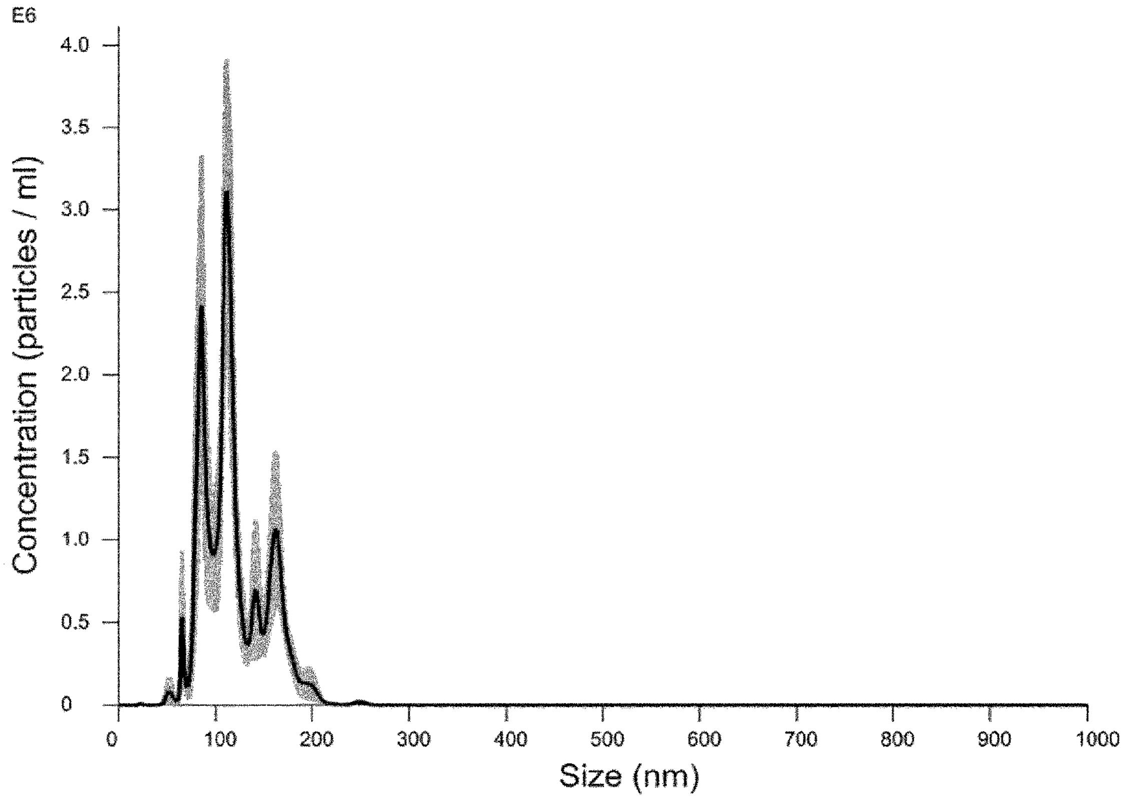
FIG. 16 is a graph showing the measurement results of the particle size and the number of fine bubbles of 2,3,3,3-tetrafluoropropylene in 1,3-dioxolane (Example 15).
Figure 17:
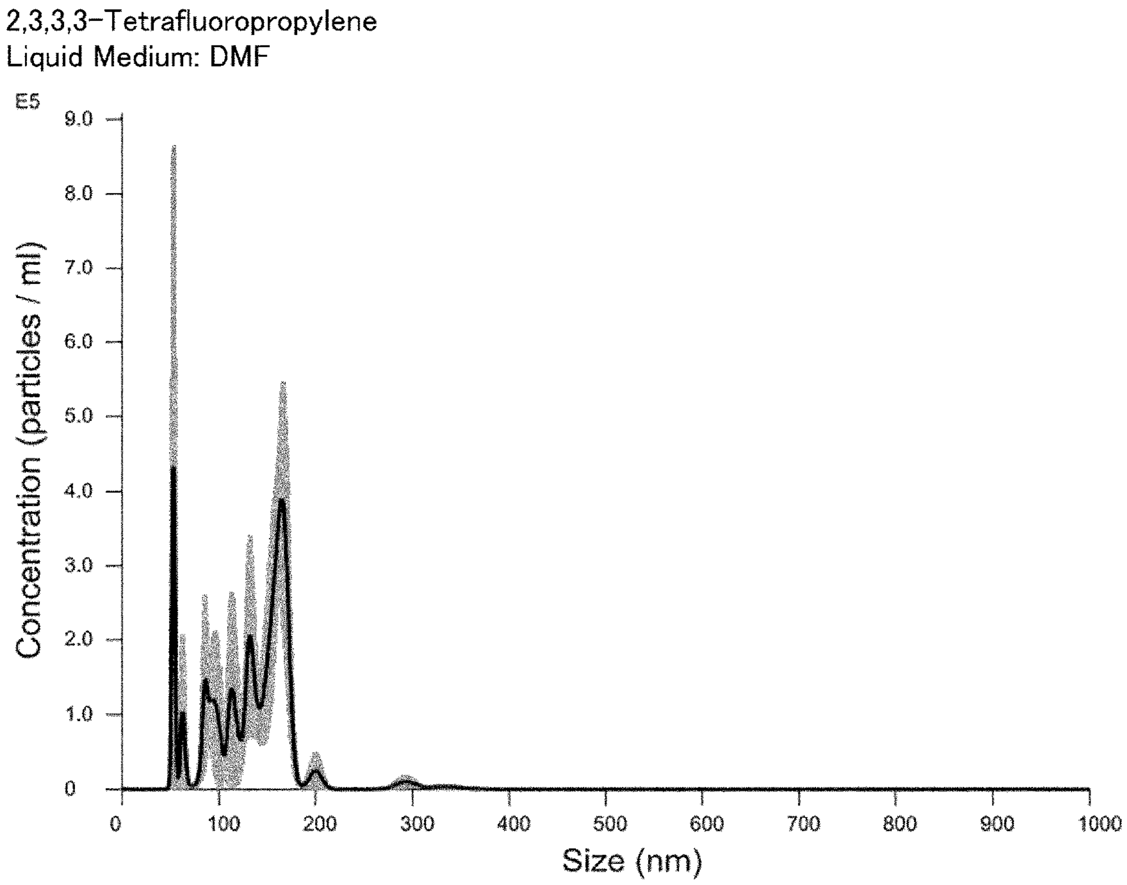
FIG. 17 is a graph showing the measurement results of the particle size and the number of fine bubbles of 2,3,3,3-tetrafluoropropylene in DMF.
Figure 18:
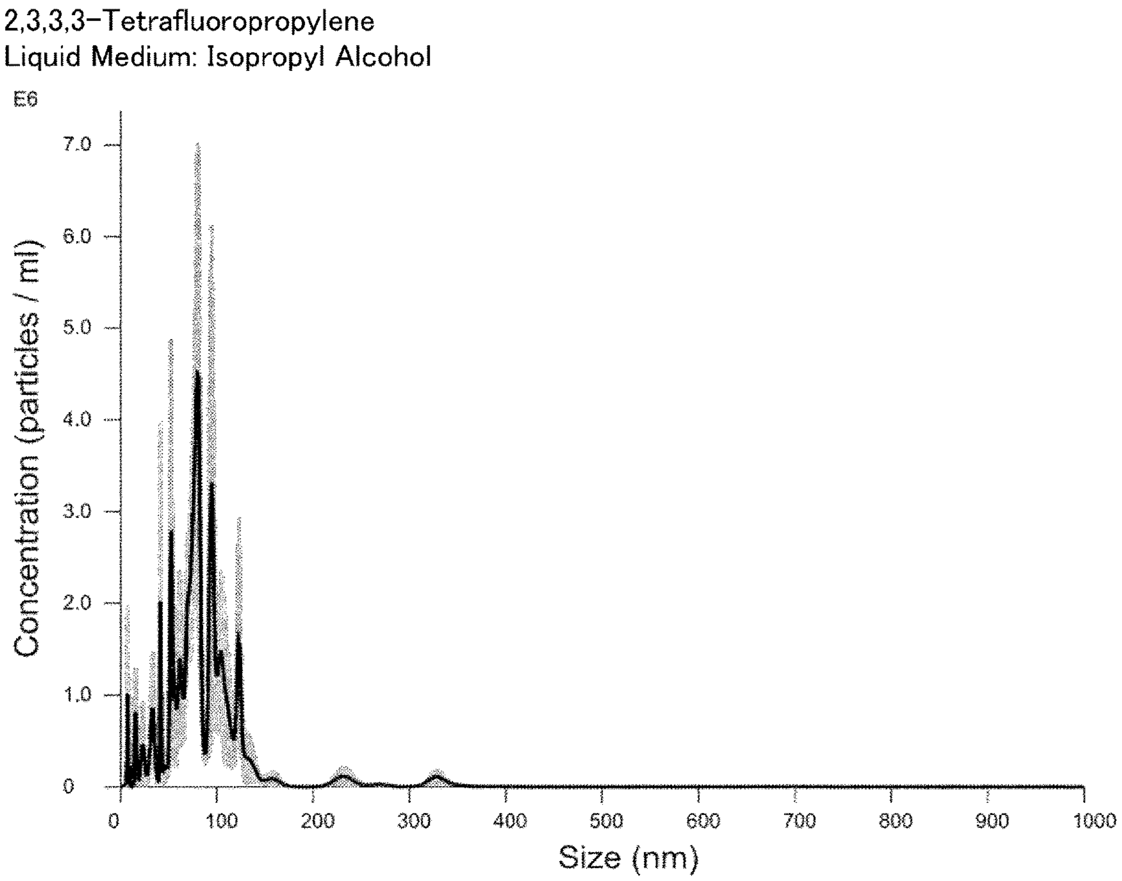
FIG. 18 is a graph showing the measurement results of the particle size and the number of fine bubbles of 2,3,3,3-tetrafluoropropylenein isopropyl alcohol (Example 15).
Figure 19:
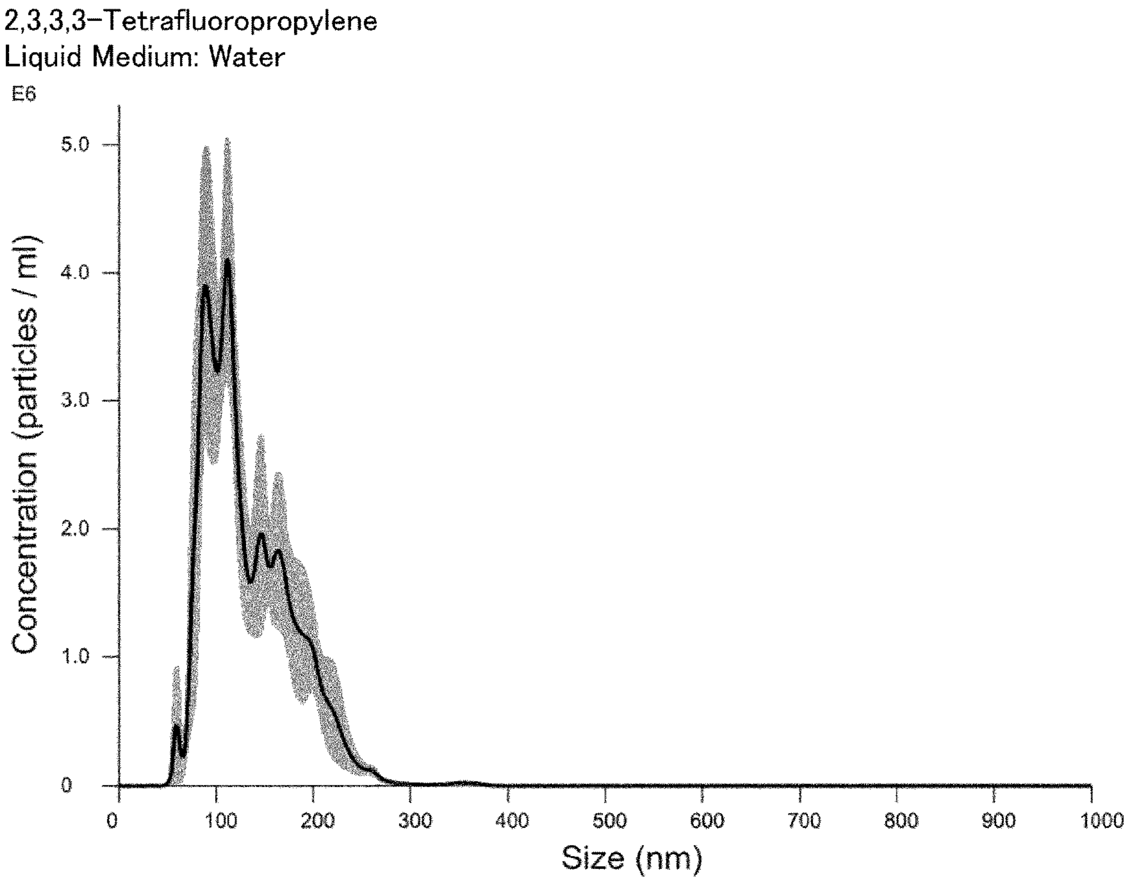
FIG. 19 is a graph showing the measurement results of the particle size and the number of fine bubbles of 2,3,3,3-tetrafluoropropylene in water (Example 15).
Figure 20:
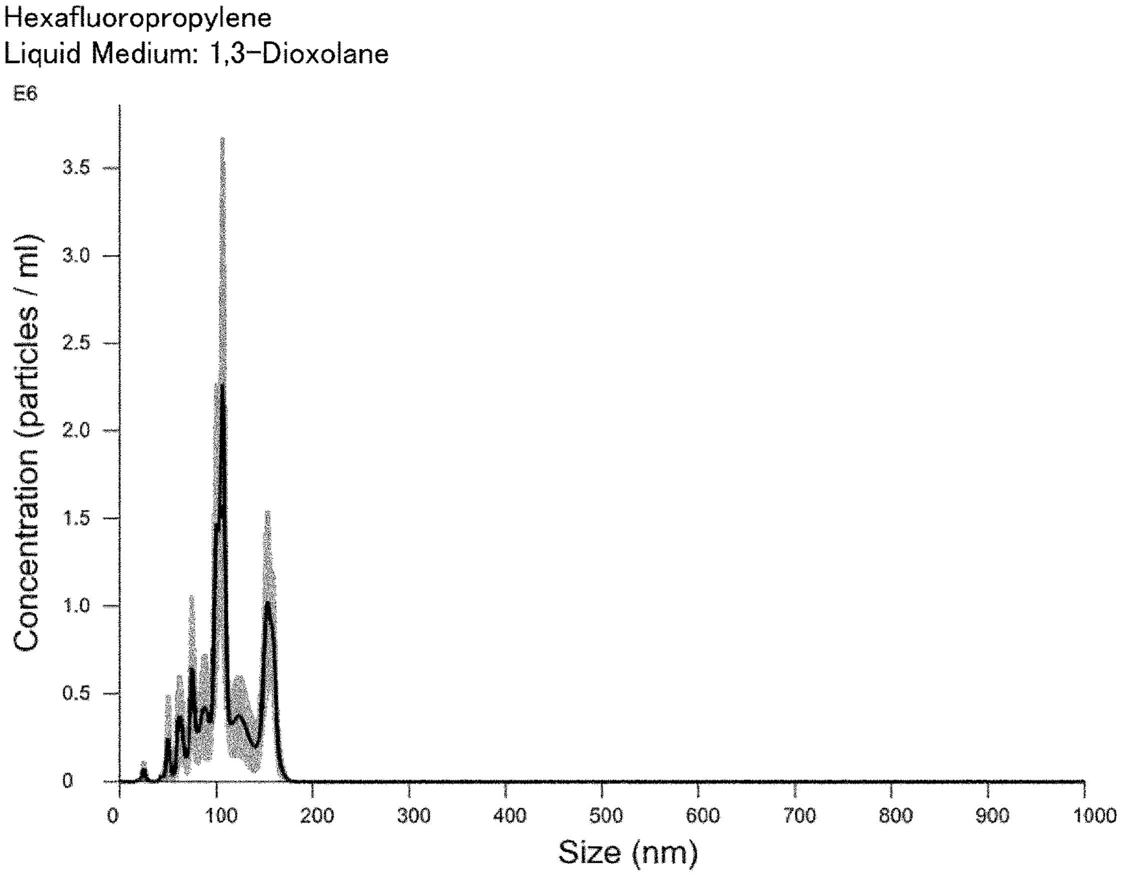
FIG. 20 is a graph showing the measurement results of the particle size and the number of fine bubbles of hexafluoropropylene in 1,3-dioxolane (Example 15).
Figure 21:
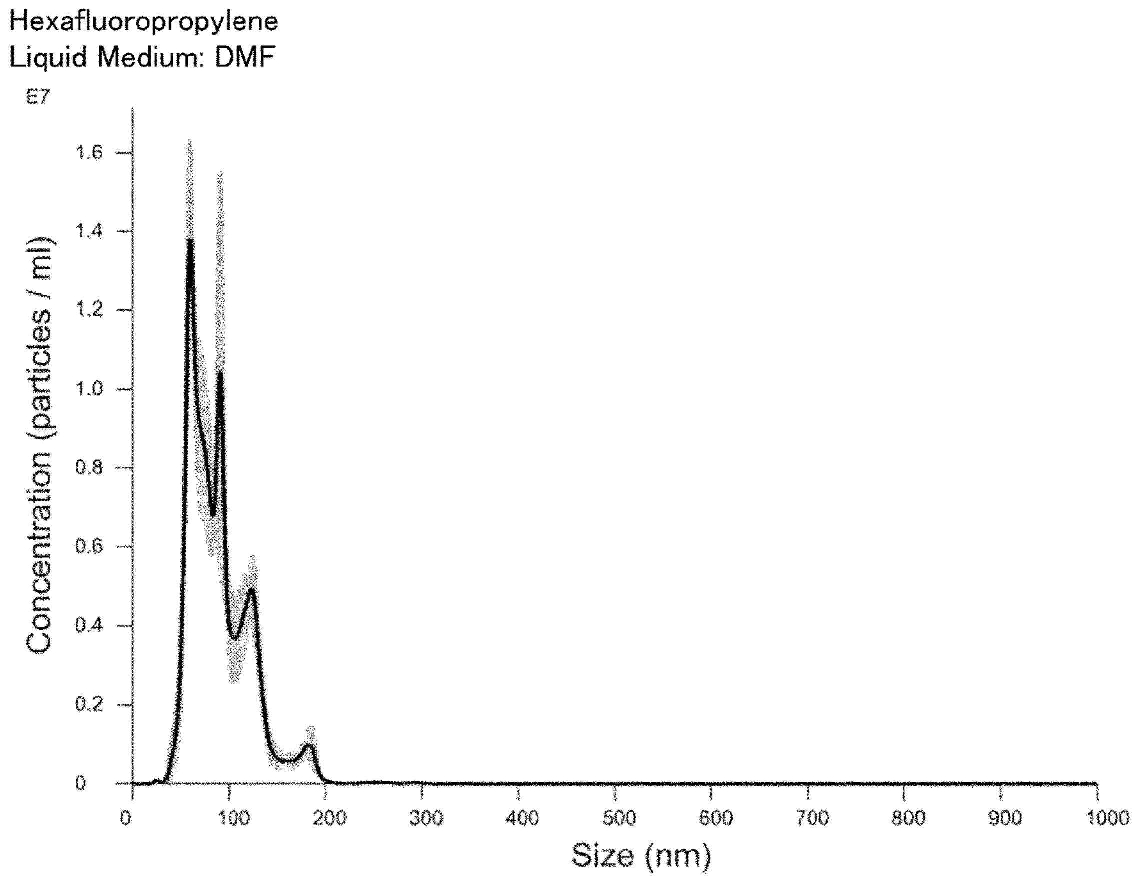
FIG. 21 is a graph showing the measurement results of the particle size and the number of fine bubbles of hexafluoropropylene in DMF (Example 15).
Figure 22:
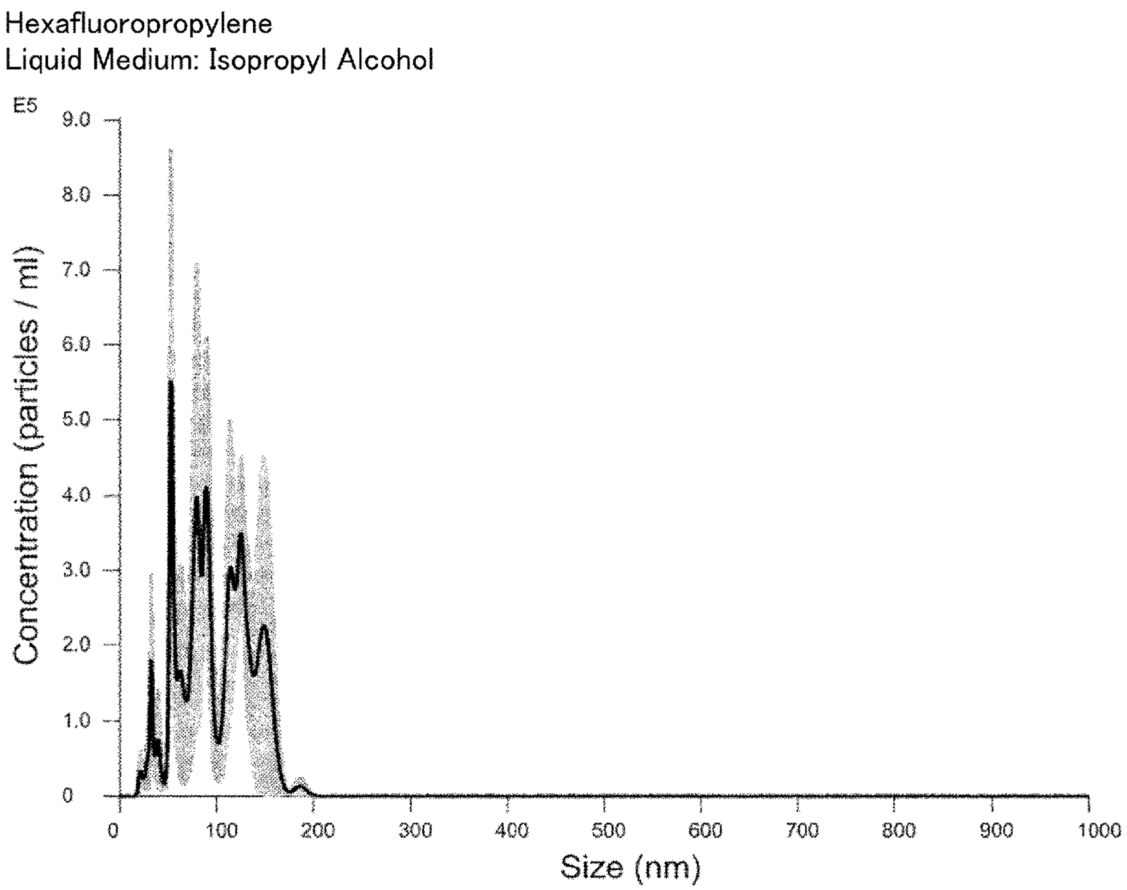
FIG. 22 is a graph showing the measurement results of the particle size and the number of fine bubbles of hexafluoropropylene in isopropyl alcohol (Example 15).
Figure 23:
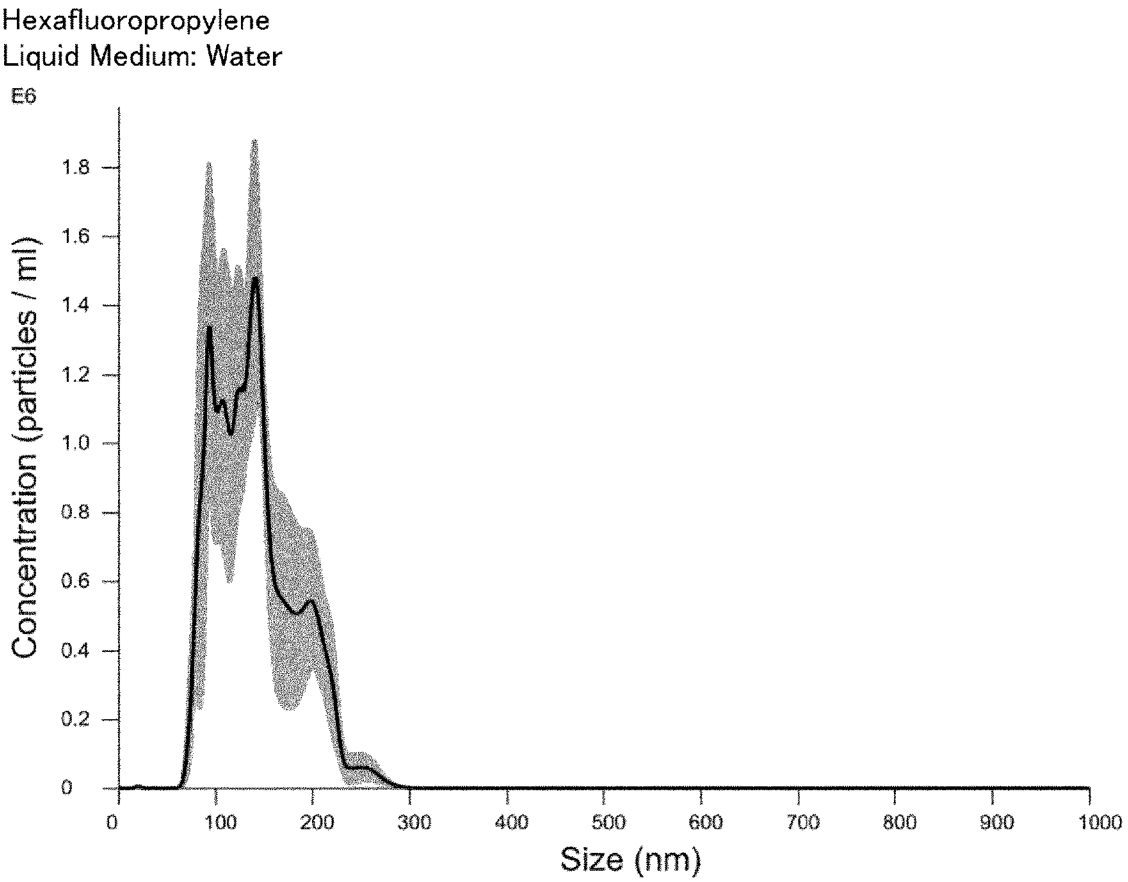
FIG. 23 is a graph showing the measurement results of the particle size and the number of fine bubbles of hexafluoropropylene in water (Example 15).
Figure 24:
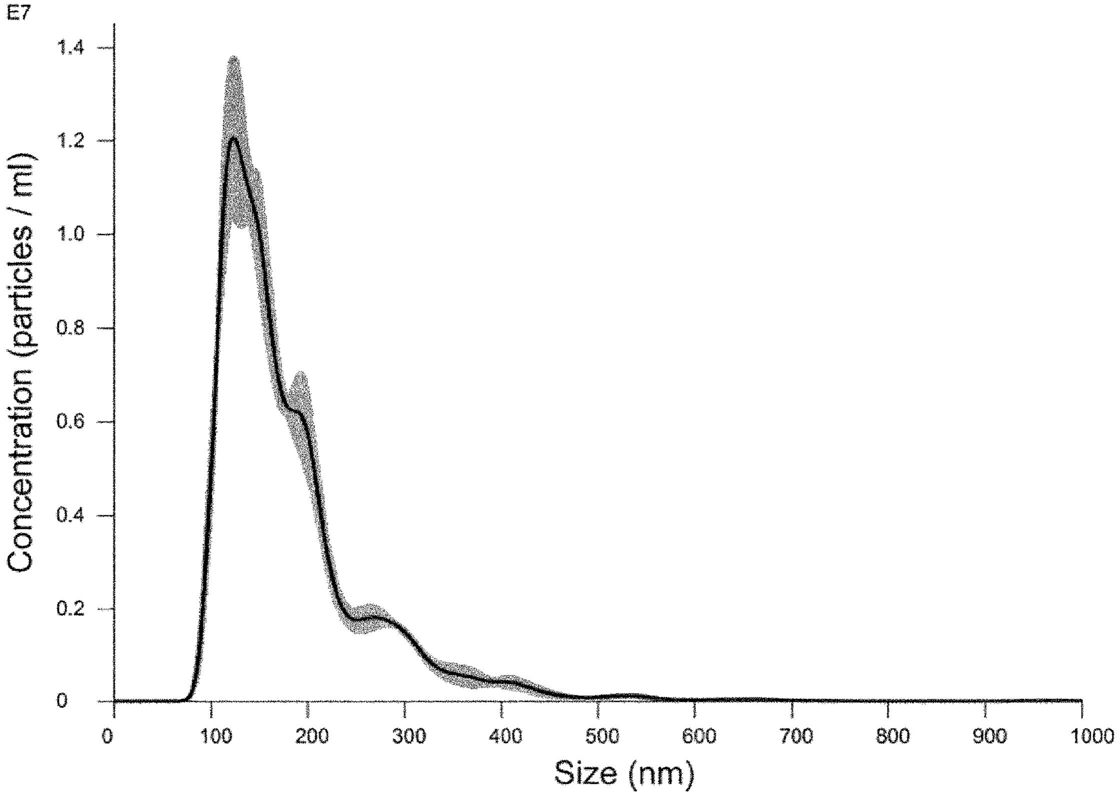
FIG. 24 is a graph showing the measurement results of the particle size and the number of fine bubbles of 1-bromo-1-fluoroethylene in water (Example 15).
Figure 25:
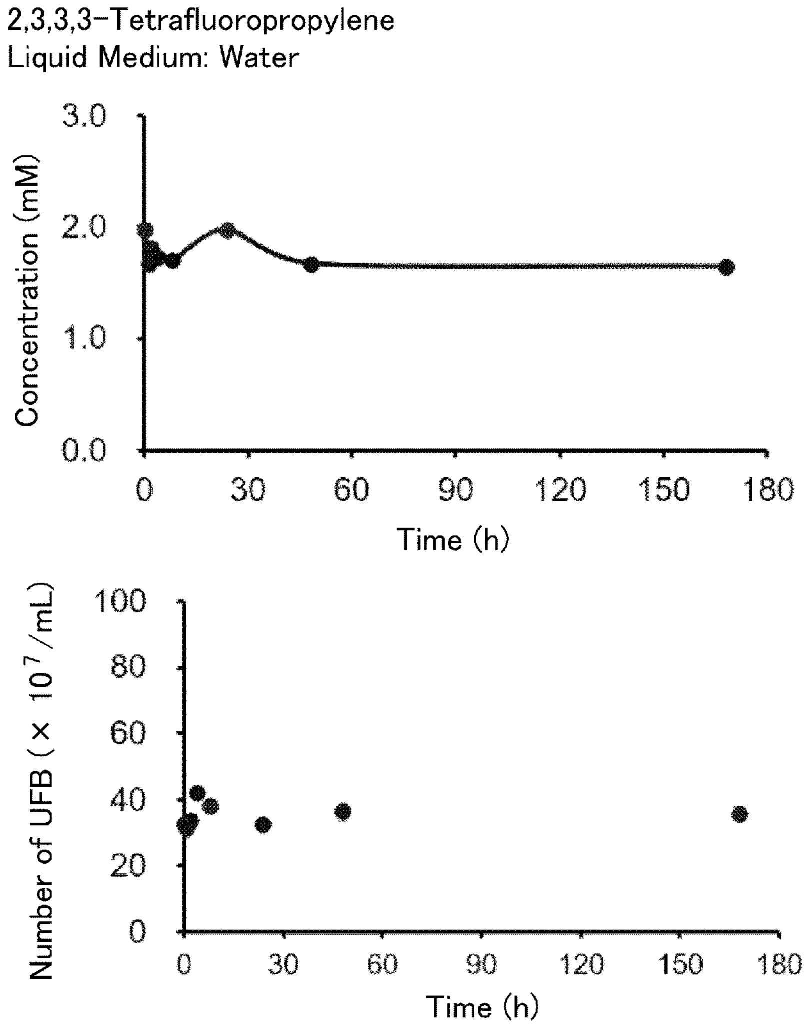
FIG. 25 is a graph showing a change over time in the concentration of 2,3,3,3-tetrafluoropropylene, and a change over time in the number of ultrafine bubbles in water (Example 16).
Figure 26:
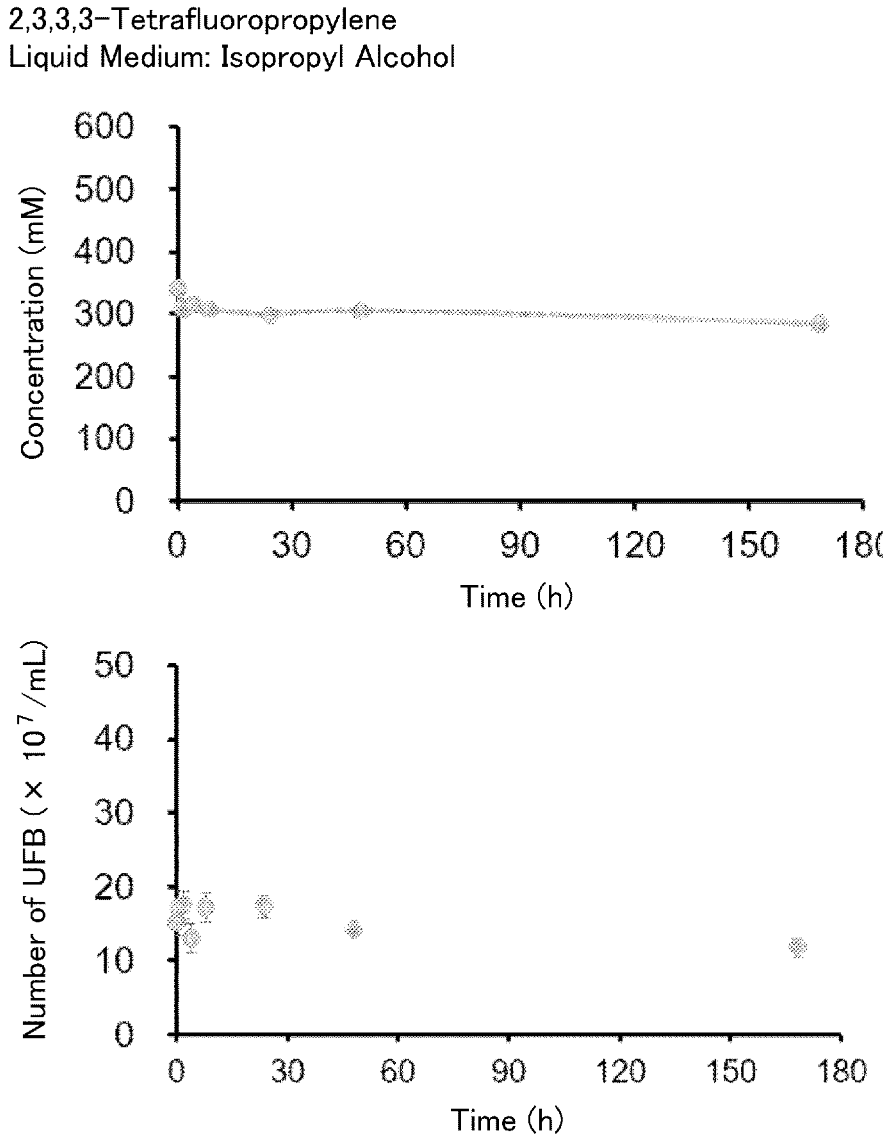
FIG. 26 is a graph showing a change over time in the concentration of 2,3,3,3-tetrafluoropropylene, and a change over time in the number of ultrafine bubbles in isopropyl alcohol (Example 16).
Figure 27:
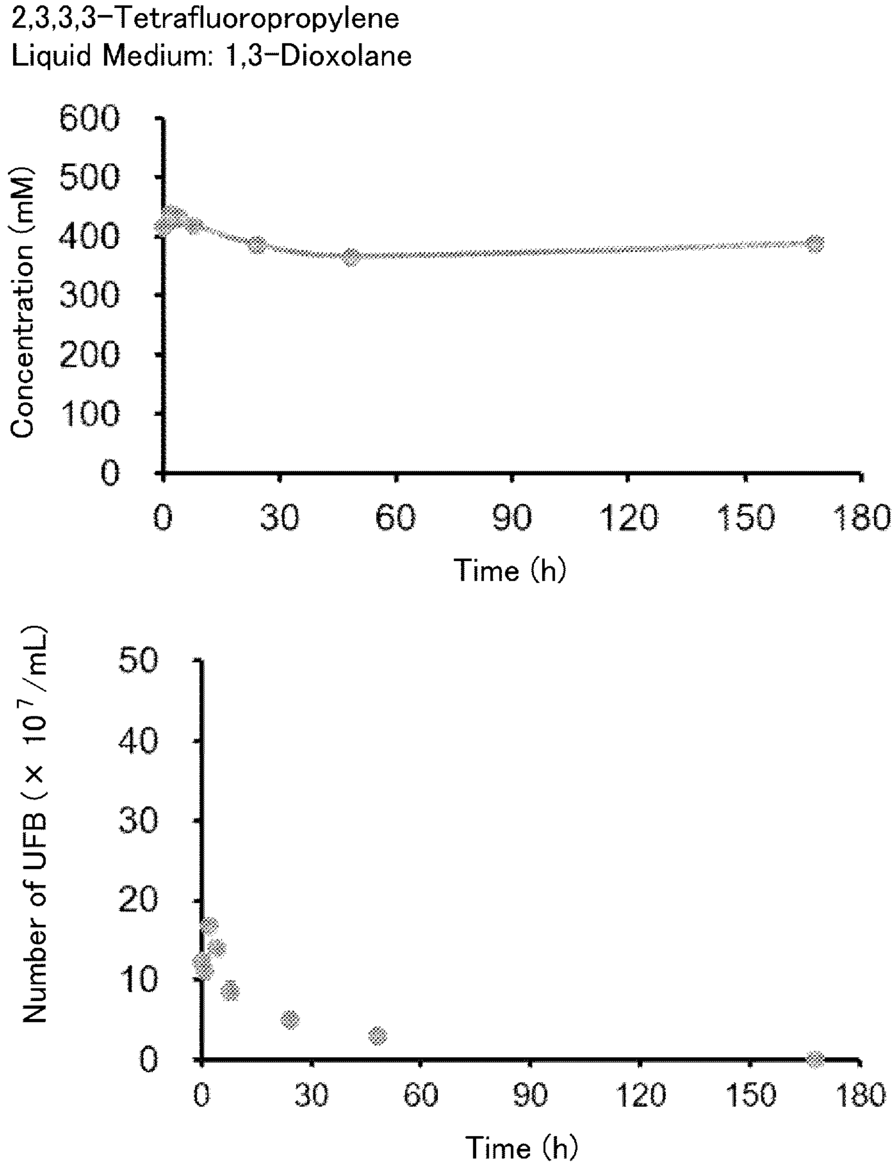
FIG. 27 is a graph showing a change over time in the concentration of 2,3,3,3-tetrafluoropropylene, and a change over time in the number of ultrafine bubbles in 1,3-dioxolane (Example 16).
Figure 28:
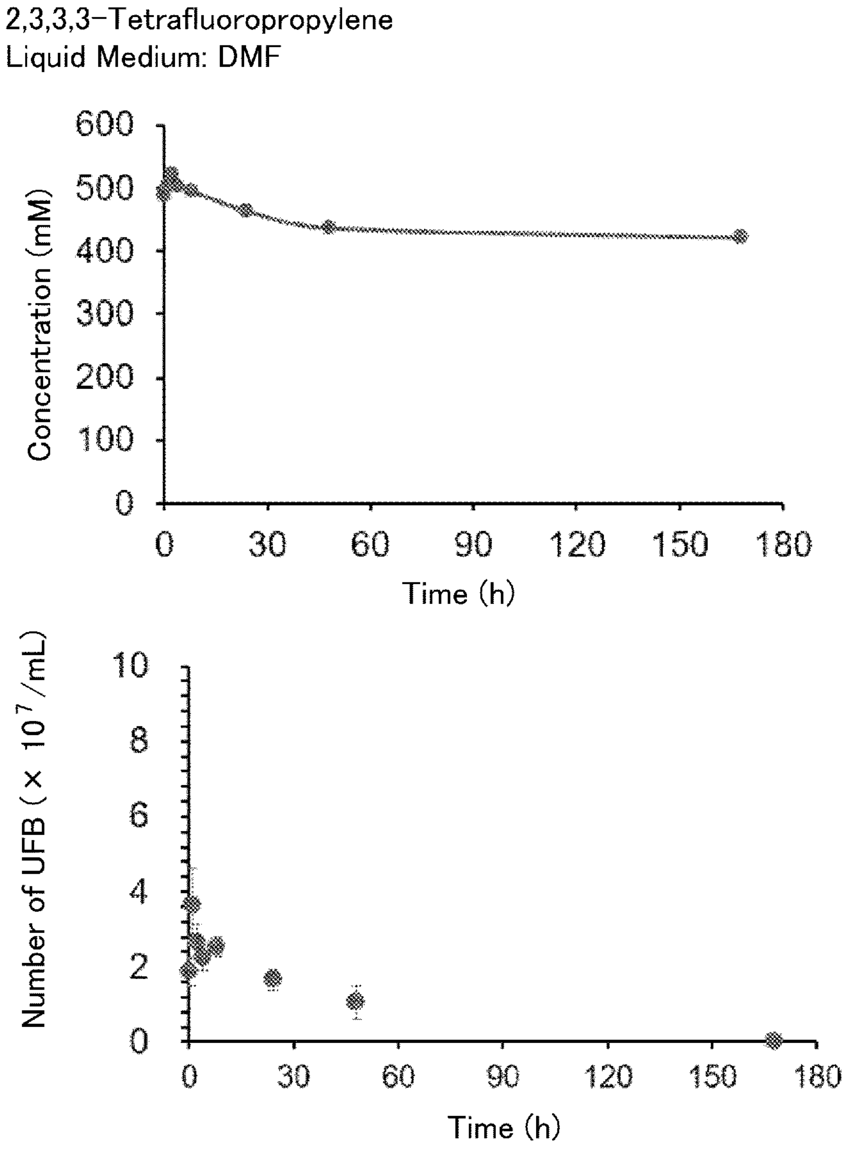
FIG. 28 is a graph showing a change over time in the concentration of 2,3,3,3-tetrafluoropropylene, and a change over time in the number of ultrafine bubbles in DMF (Example 16).
Figure 29:
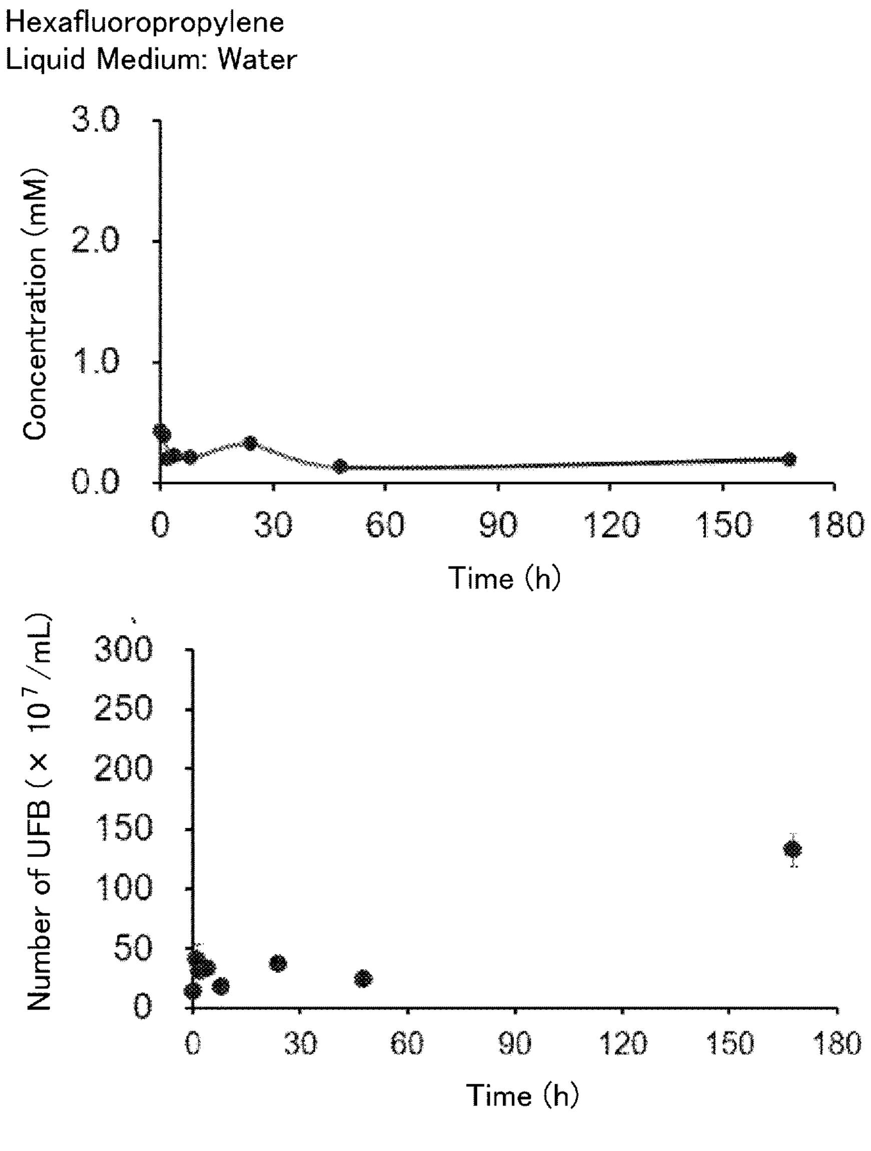
FIG. 29 is a graph showing a change over time in the concentration of hexafluoropropylene, and a change over time in the number of ultrafine bubbles in water (Example 16).
Figure 30:
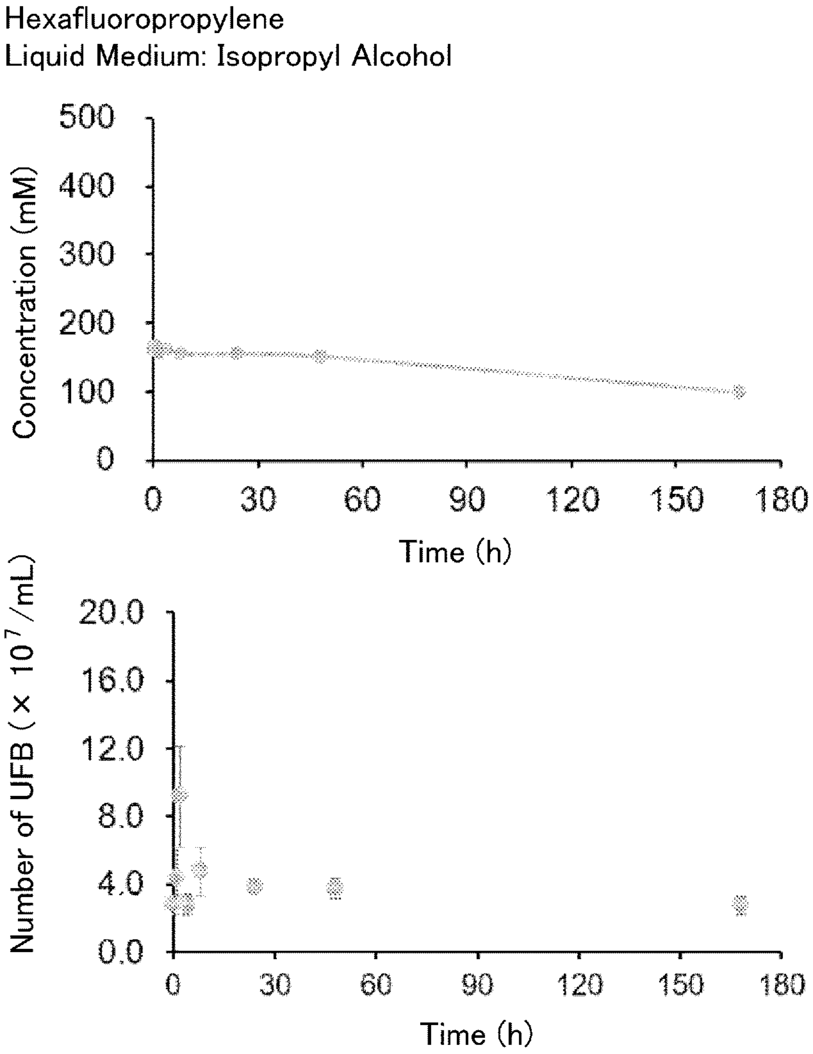
FIG. 30 is a graph showing a change over time in the concentration of hexafluoropropylene, and a change over time in the number of ultrafine bubbles in isopropyl alcohol (Example 16).
Figure 31:
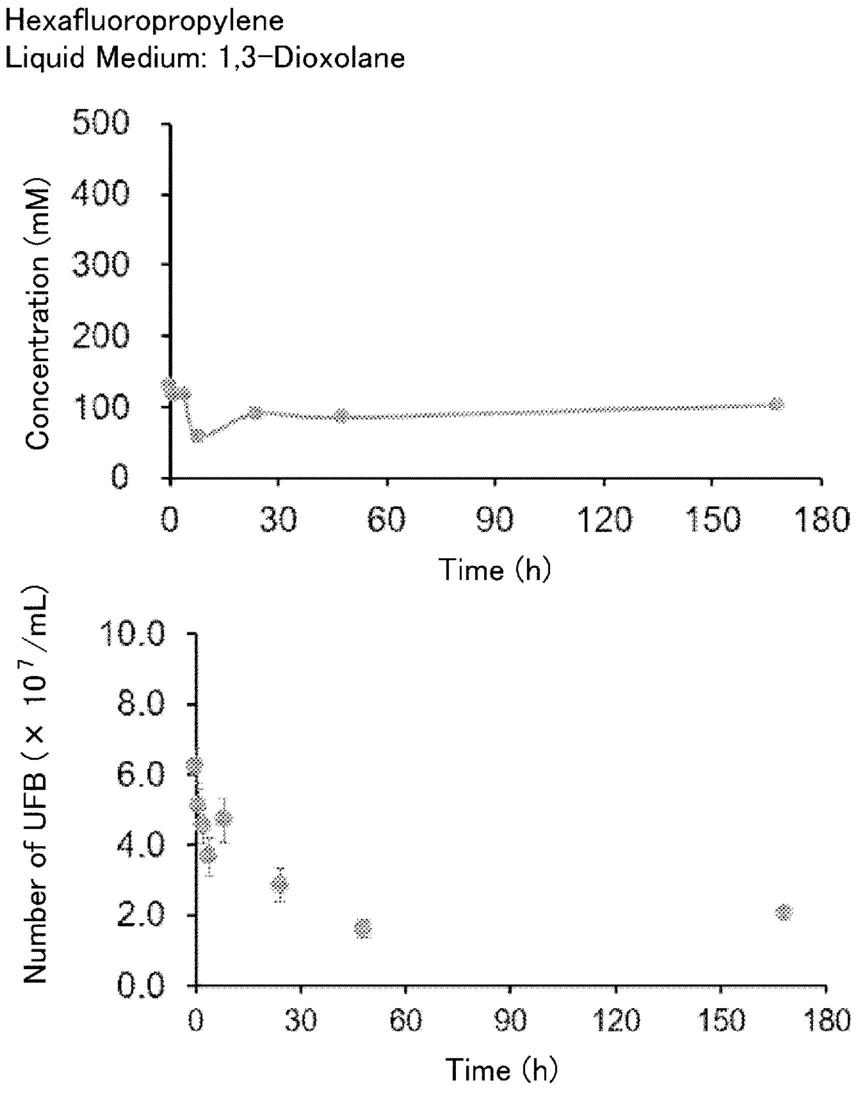
FIG. 31 is a graph showing a change over time in the concentration of hexafluoropropylene, and a change over time in the number of ultrafine bubbles in 1,3-dioxolane (Example 16).
Figure 32:
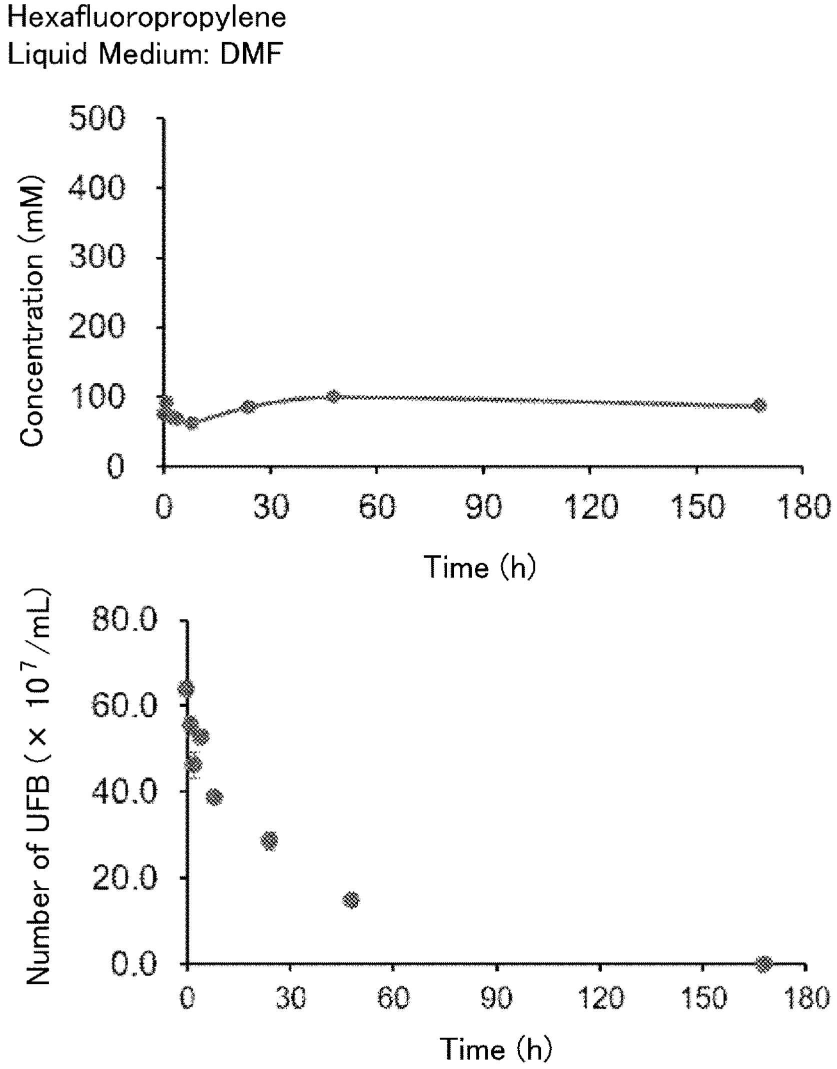
FIG. 32 is a graph showing a change over time in the concentration of hexafluoropropylene, and a change over time in the number of ultrafine bubbles in DMF (Example 16).
Figure 33:
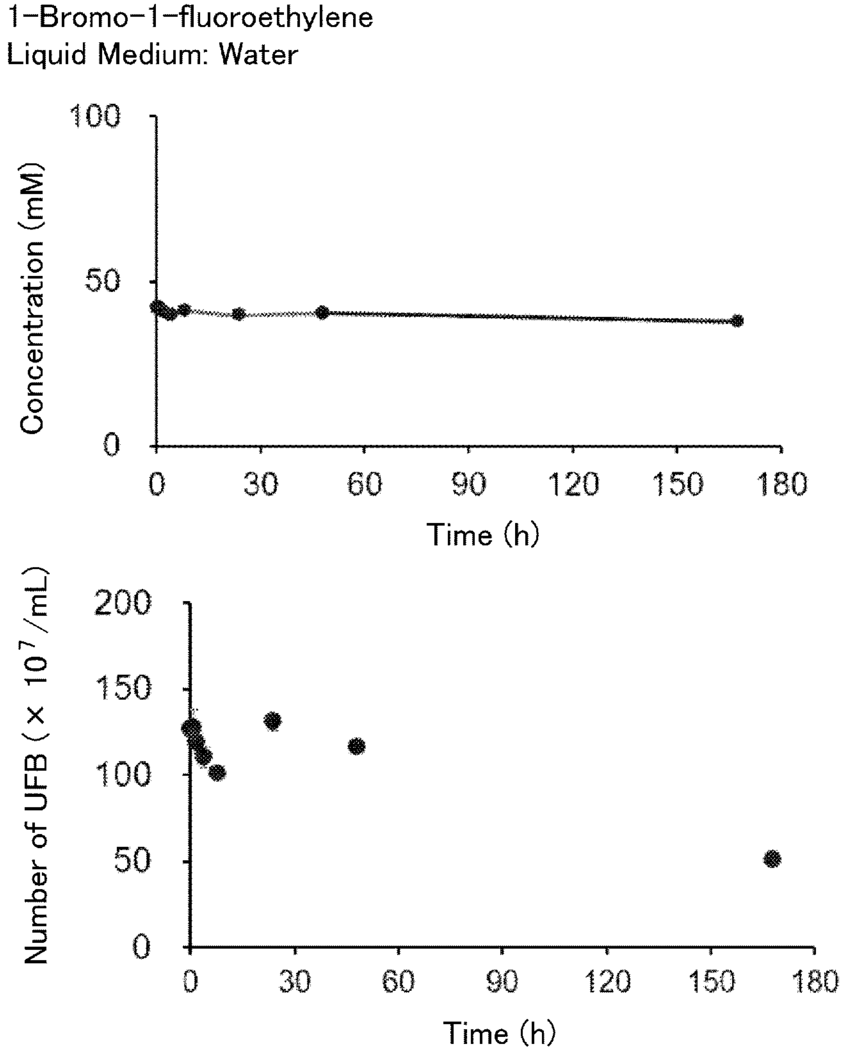
FIG. 33 is a graph showing a change over time in the concentration of 1-bromo-1-fluoroethylene, and a change over time in the number of ultrafine bubbles in water (Example 16).

In each Example, the apparatuses and conditions outlined in FIGS. 1 to 3 were used. The straight line in the figures represents a pipeline, and the straight arrow represents the direction of fluid flow.

In the apparatus shown in FIG. 1, the reaction liquid taken out from the internal-light-irradiation reactor is fed to a fine bubble generator (to which a VdF cylinder is attached, as shown in FIG. 1). The fine bubbles of VdF generated by the apparatus are incorporated into the reaction liquid, and this liquid is supplied to the reactor to circulate the reaction liquid.

In the apparatus shown in FIG. 2, the reaction liquid taken out from the internal-light-irradiation reactor and VdF gas are mixed, and the mixed fluid (gas-liquid slug flow) is supplied to the reactor to circulate the reaction liquid.

In the apparatus shown in FIG. 3, while VdF gas bubbles are fed to the reaction liquid by a Kerami filter (cylindrical gas-injection tube), the reaction liquid taken out from the internal-light-irradiation reactor is re-supplied to the reactor to circulate the reaction liquid.

The reaction liquid is circulated from the reactor back to the reactor through a back-pressure regulator (in the figures, BPR). The internal-light-irradiation reactor is equipped with a 100 W Hg lamp as a light source.

Example 1

A mixture solution of 1,3-dioxolane (48 mL) and acetone (12 mL) was introduced into a Pyrex (registered trademark) reactor in a hot water bath by using the apparatus outlined in FIG. 1. The internal temperature was then set to 40° C. While the solution was circulated at a rate of 30 mL/min by using a pump (which was an HPLC pump, as described in the figures) under irradiation with a 100 W mercury lamp, VdF formed into fine bubbles with a fine bubble generator was introduced at a rate of 4.0 mL/min. After 2 hours, the solution was analyzed by F-NMR. An adduct was obtained at a yield of 11%. Table 1 shows the generation ratio.

Example 2

1,3-Dioxolane (60 mL) and Irgacure 127 (63 mg, 0.2 μmol) were introduced into a Pyrex (registered trademark) reactor in a hot water bath by using the same apparatus as that in Example 1. The internal temperature was then set to 40° C. While the solution was circulated at a rate of 30 mL/min by using a pump (which was an HPLC pump as described in the figures) under irradiation with a 100 W mercury lamp, VdF formed into fine bubbles with a fine bubble generator was introduced at a rate of 4.0 mL/min. After 2 hours, the solution was analyzed by F-NMR. An adduct was obtained at a yield of 44%. Table 1 shows the generation ratio.

Example 3

The procedure was repeated in the same manner as in Example 2, except that the reaction time was changed to 24 hours, thereby obtaining an adduct at a yield of 87%. Table 1 shows the generation ratio.

TABLE 1

| | A | B | C | D |
|---|---|---|---|---|
| Example 1 | 17 | 3 | 5 | 1 |
| Example 2 | 14 | 3 | 3 | 1 |
| Example 3 | 67 | 13 | 6 | 1 |

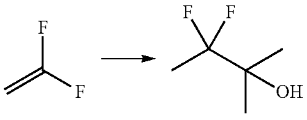

E

-continued

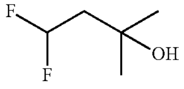

F

Examples 4 and 5

Example 4

The procedure was repeated in the same manner as in Example 1, except that 1,3-dioxolane was changed to isopropyl alcohol, thereby obtaining an adduct at an yield of 32%. Table 2 shows the generation ratio.

Example 5

The procedure was repeated in the same manner as in Example 2, except that 1,3-dioxolane was changed to isopropyl alcohol, thereby obtaining an adduct at an yield of 14%. Table 2 shows the generation ratio.

TABLE 2

| | E | F |
|---|---|---|
| Example 4 | 2 | 1 |
| Example 5 | 2 | 1 |

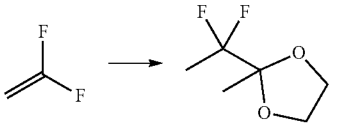

G

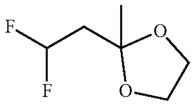

H

Example 6

The procedure was repeated in the same manner as in Example 1, except that 1,3-dioxolane was changed to 2-methyl-1,3-dioxolane, thereby obtaining adducts G and H. Table 3 shows the generation ratio.

TABLE 3

| | G | H |
|---|---|---|
| Example 6 | 3 | 1 |

Example 7

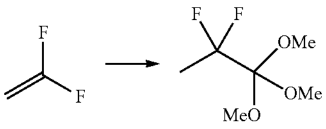

I

-continued

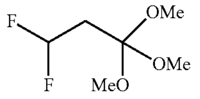

J

The procedure was repeated in the same manner as in Example 1, except that 1,3-dioxolane was changed to methyl orthoformate (48 mL), thereby obtaining an adduct at an yield of 22%.

Example 8

The procedure was repeated in the same manner as in Example 1, except that acetone was not added, and the amount of 1,3-dioxolane was changed to 60 mL, thereby obtaining an adduct at an yield of 12%. Table 4 shows the generation ratio.

TABLE 4

| | A | B | C | D |
|---|---|---|---|---|
| Example 8 | 4 | 1 | 0 | 0 |

Example 9

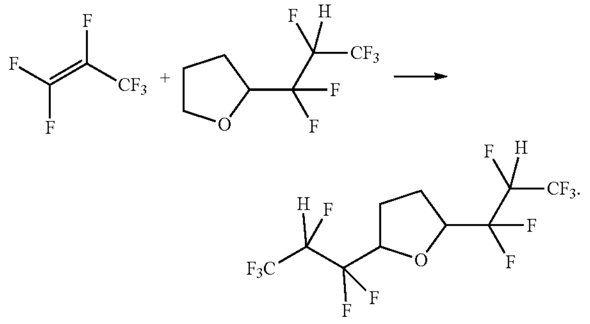

A mixture solution of 2-(2H-hexafluoropropyl) tetrahydrofuran (18.5 g), acetone (0.4 g), and acetonitrile (35 mL) was introduced into the reactor outlined in FIG. 1. The internal temperature was then set to −30° C. While the solution was circulated at a rate of 30 mL/min under irradiation with a 100 W mercury lamp, hexafluoropropene in the form of fine bubbles was introduced thereto. After 2 hours, the solution was analyzed by F-NMR. Bis-2,5-(2H-hexafluoropropyl) tetrahydrofuran was obtained at a yield of 90%.

Examples 10 and 11

Example 10

The procedure was repeated in the same manner as in Example 1, except that the apparatus was changed to the apparatus outlined in FIG. 2, thereby obtaining an adduct at a yield of 9%. Table 5 shows the generation ratio.

Example 11

The procedure was repeated in the same manner as in Example 1, except that the apparatus was changed to the apparatus equipped with a Kerami filter outlined in FIG. 3, thereby obtaining an adduct at a yield of 3%. Table 5 shows the generation ratio.

TABLE 5

| | A | B | C | D |
|---|---|---|---|---|
| Example 10 | 7 | 3 | 1 | 1 |
| Example 11 | 14 | 6 | 1 | 1 |

Example 12: Measurement of the Particle Size and the Number of Fine Bubbles of VdF The particle size of the bubbles generated by a fine bubble generator was measured with a NanoSight nanoparticle analyzer (Quantum Design Japan). The measurement conditions were as follows.

Liquid medium: water, isopropyl alcohol, 1,3-dioxolane, and DMF

Gas: VdF

Nanobubble ejection pressure: 3.0 MPa

Liquid flow rate: 28 mL/minute

Gas flow rate: 14 mL/minute

The measurement results confirmed the existence of bubbles based on the measurable smallest particle size of 10 nm. FIGS. 4 to 7 show the results. In the figures, the horizontal axis indicates the particle size of bubbles, and the vertical axis indicates the number of bubbles by individual particle size per milliliter of a gas-liquid mixed fluid. Substantially all of the bubbles (100%) formed had a particle size of 10 to 500 nm, and the bubbles with a particle size of 50 to 500 nm accounted for at least 95% of the total number of bubbles.

Example 13: Observation Over Time of Ultrafine Bubbles of VdF 50 mL of a liquid medium used for measurement (water, isopropyl alcohol, 1,3-dioxolane, or DMF) was placed in a 100-mL Duran bottle; and ultrasonic degasification and three instances of Ar replacement were performed to remove dissolved gas in the liquid medium.

Using the same apparatus as that used in Example 1, the reaction temperature was set at 30° C., and the reaction solution was pumped at an actual flow rate of 28 mL/min and VdF at a rate of 14 mL/min, followed by measuring the saturated concentration by a GC-FID. The number and concentration of ultrafine bubbles were measured after 0, 1, 2, 4, 8, 24, 48, and 168 hours from the time point at which the VdF concentration reached saturation, which was taken as "0." FIGS. 8 to 15 show the results of the observation over time.

Example 14

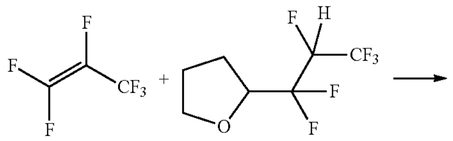

-continued

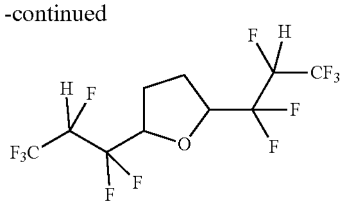

A mixture solution of 2-(2H-hexafluoropropyl) tetrahydrofuran (18.5 g), acetone (0.4 g), and acetonitrile (35 mL) was introduced into a reactor. The internal temperature was then set to −30° C. While the solution was circulated at a rate of 30 mL/min under irradiation with a 100 W mercury lamp, hexafluoropropene in the form of fine bubbles was introduced. After 2 hours, the solution was analyzed by F-NMR. Bis-2,5-(2H-hexafluoropropyl) tetrahydrofuran was obtained at a yield of 90%.

Comparative Example 1

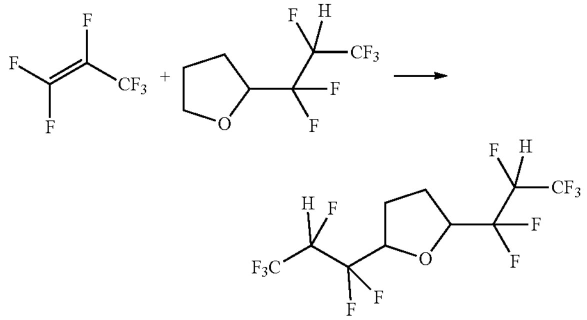

Under irradiation with a 100 W mercury lamp, the temperature was set to −30° C. to −35° C., and hexafluoropropene (5.9 g) was introduced into a solution of 2-(2H-hexafluoropropyl) tetrahydrofuran (18.5 g) and acetone (0.4 g) in acetonitrile (35 mL) inside a photoreactor. After 6 hours, the mixture was neutralized with hydrogen carbonate. The reaction mixture was dried and purified by distillation, thereby obtaining bis-2,5-(2H-hexafluoropropyl) tetrahydrofuran with a boiling point of 98° C. to 100° C./0.6 kPa (12.4 g, yield: 85%). At a point of 2 hours during the reaction, the yield was 60%.

Example 15: Measurement of the Particle Size and the Number of Bubbles of Various Types of Fine Bubbles The particle size of the bubbles generated by a fine bubble generator was measured with a NanoSight nanoparticle analyzer (Quantum Design Japan). The measurement conditions were as follows.

Liquid medium: water, isopropyl alcohol, 1,3-dioxolane, and DMF

Gas: 2,3,3,3-tetrafluoropropylene, hexafluoropropylene, or 1-bromo-1-fluoroethylene Nanobubble ejection pressure: 3.0 MPa Liquid flow rate: 28 mL/min Gas flow rate: 14 mL/min The measurement results confirmed the existence of bubbles based on the measurable smallest particle size of 10 nm. FIGS. 16 to 24 show the results. In the figures, the horizontal axis indicates the particle size of bubbles, and the vertical axis indicates the number of bubbles by individual particle size per milliliter of a gas-liquid mixed fluid. Substantially all of the bubbles (100%) formed had a particle size of 10 to 500 nm, and the bubbles with a particle size of 50 to 500 nm accounted for at least 95% of the total number of bubbles.

Example 16: Observation Over Time of Ultrafine Bubbles of Each Type of Gas 50 mL of a liquid medium used for measurement (water, isopropyl alcohol, 1,3-dioxolane, or DMF) was placed in a 100-mL Duran bottle; and ultrasonic degassing and three instances of Ar replacement were performed to remove dissolved gas in the liquid medium.

Using the same apparatus as that used in Example 1, the reaction temperature was set to 20 to 30° C., and the reaction solution was pumped at an actual flow rate of 28 mL/min and 2,3,3,3-tetrafluoropropylene, hexafluoropropylene, or 1-bromo-1-fluoroethylene at a rate of 14 mL/min, followed by measuring the saturated concentration by a GC-FID. The number and concentration of ultrafine bubbles were measured after 0, 1, 2, 4, 8, 24, 48, and 168 hours from the time point at which the concentration reached saturation, which was taken as "0." FIGS. 25 to 33 show the results.

The invention claimed is:

1. A composition comprising a fluorine-containing olefin, the composition comprising:

(1) a fluorine-containing olefin, the fluorine-containing olefin excluding vinylidene fluoride, and (2) a liquid medium, wherein at least a portion of the fluorine-containing olefin in a form of fine bubbles is dispersed in the liquid medium; and wherein the fine bubbles are in such a form that the percentage of the number of bubbles having a particle size within a range of 5 nm to 100 μm is 90% or more of the total number of the bubbles.

2. The composition comprising the fluorine-containing olefin according to claim 1, wherein the fluorine-containing olefin is a compound represented by formula (3):

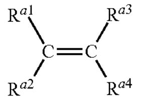

(3)

wherein $R^{a1}$, $R^{a2}$, $R^{a3}$, and $R^{a4}$ are the same or different and each represent a hydrogen atom, a fluorine atom, a chlorine atom, or a fluoroalkyl group, with the proviso that of $R^{a1}$, $R^{a2}$, $R^{a3}$, and $R^{a4}$, at least one is a fluorine atom.

3. The composition comprising the fluorine-containing olefin according to claim 1, wherein the liquid medium comprises at least one member selected from the group consisting of water an organic solvent that is a poor solvent for the fluorine-containing olefin represented by formula (3).

* * * * *